(12) United States Patent  (10) Patent No.: US 7,628,801 B2
Westlund et al.  (45) Date of Patent: Dec. 8, 2009

(54) CORONARY VEIN LEADS HAVING AN ATRAUMATIC TIP AND METHOD THEREFOR

(75) Inventors: Randy Westlund, Minneapolis, MN (US); Bruce Tockman, Scandia, MN (US); Christina Repasky, Maplewood, MN (US); Lyle A. Bye, Lino Lakes, MN (US); Brian D. Soltis, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 854 days.

(21) Appl. No.: 10/128,997

(22) Filed: Apr. 23, 2002

(65) Prior Publication Data

US 2003/0109914 A1   Jun. 12, 2003

Related U.S. Application Data

(63) Continuation-in-part of application No. 09/651,340, filed on Aug. 30, 2000, now Pat. No. 6,584,362.

(51) Int. Cl.
*A61F 7/00*   (2006.01)

(52) U.S. Cl. ...................................... 607/112

(58) Field of Classification Search ................. 607/112, 607/122, 123, 125, 5; 600/374
See application file for complete search history.

(56) References Cited

U.S. PATENT DOCUMENTS

| 4,402,330 | A |   | 9/1983  | Lindemans  ................. 128/786 |
| 4,577,639 | A |   | 3/1986  | Simon et al.  ................. 128/709 |
| 4,932,407 | A | * | 6/1990  | Williams  ........................ 607/5 |
| 4,958,632 | A |   | 9/1990  | Duggan  ................. 128/419 PG |
| 5,076,272 | A |   | 12/1991 | Ferek-Petric  ................. 128/419 |
| 5,318,593 | A |   | 6/1994  | Duggan  .......................... 607/9 |
| 5,476,498 | A |   | 12/1995 | Ayers  ........................ 607/122 |
| 5,531,781 | A | * | 7/1996  | Alferness et al.  ............ 607/122 |
| 5,545,204 | A |   | 8/1996  | Cammilli et al.  ............ 607/123 |
| 5,674,274 | A | * | 10/1997 | Morgan et al.  ............... 607/123 |
| 5,683,445 | A |   | 11/1997 | Swoyer  ....................... 607/125 |
| 5,755,766 | A | * | 5/1998  | Chastain et al.  ............. 607/122 |
| 5,871,531 | A |   | 2/1999  | Struble  ........................ 607/126 |

(Continued)

FOREIGN PATENT DOCUMENTS

DE   20010369   9/2000

(Continued)

OTHER PUBLICATIONS

"U.S. Appl. No. 09/651,340 Advisory Action mailed Dec. 16, 2002", 3 pgs.

(Continued)

*Primary Examiner*—George Manuel
(74) *Attorney, Agent, or Firm*—Faegre & Benson, LLP

(57) ABSTRACT

A lead having an atraumatic tip is adapted for implantation on or about the heart within the coronary vasculature and for connection to a signal generator. The lead is constructed and arranged so that when it is implanted, the electrodes are housed in the coronary vasculature and are biased toward a vessel wall by a preformed biased portion. Near the distal end, the lead has an optional tapered portion and a flexible portion, where the flexible portion is more flexible than the biased portion.

31 Claims, 16 Drawing Sheets

U.S. PATENT DOCUMENTS

| | | | |
|---|---|---|---|
| 5,897,577 A | | 4/1999 | Cinbis et al. .................. 607/28 |
| 5,908,385 A | * | 6/1999 | Chechelski et al. ......... 600/374 |
| 5,925,073 A | | 7/1999 | Chastain et al. ............. 607/122 |
| 6,021,354 A | | 2/2000 | Warman et al. ............. 607/123 |
| 6,070,104 A | * | 5/2000 | Hine et al. .................. 607/123 |
| 6,085,117 A | * | 7/2000 | Griffin et al. .................... 607/5 |
| 6,148,237 A | * | 11/2000 | Das ............................. 607/122 |
| 6,161,029 A | | 12/2000 | Spreigl et al. ............... 600/381 |
| 6,292,693 B1 | | 9/2001 | Darvish et al. .................. 607/9 |
| 6,325,797 B1 | * | 12/2001 | Stewart et al. ................ 606/41 |
| 6,363,288 B1 | | 3/2002 | Bush et al. .................. 607/122 |
| 6,377,856 B1 | | 4/2002 | Carson ........................ 607/122 |
| 6,385,492 B1 | | 5/2002 | Ollivier et al. .............. 607/122 |
| 6,556,873 B1 | | 4/2003 | Smits |
| 6,584,362 B1 | | 6/2003 | Scheiner et al. ............. 607/122 |
| 6,662,055 B1 | * | 12/2003 | Prutchi ....................... 607/122 |
| 6,714,823 B1 | * | 3/2004 | De Lurgio et al. .......... 607/122 |
| 6,922,589 B2 | | 7/2005 | Stahmann et al. |
| 7,058,449 B2 | | 6/2006 | Stahmann et al. |
| 7,123,951 B2 | * | 10/2006 | Fuimaono et al. ........... 600/374 |
| 7,139,614 B2 | | 11/2006 | Scheiner et al. |
| 2002/0055764 A1 | | 5/2002 | Malonek et al. ............. 607/122 |
| 2003/0109914 A1 | | 6/2003 | Westlund et al. ............ 607/122 |
| 2003/0176894 A1 | | 9/2003 | Stahmann et al. .............. 607/9 |
| 2003/0195603 A1 | | 10/2003 | Scheiner et al. ............. 607/122 |
| 2007/0067008 A1 | | 3/2007 | Scheiner et al. |

FOREIGN PATENT DOCUMENTS

| | | |
|---|---|---|
| EP | 0488512 | 10/1990 |
| EP | 0951920 | 10/1999 |
| JP | 5-049701 | 3/1993 |
| WO | WO-0218006 A2 | 3/2002 |

OTHER PUBLICATIONS

"U.S. Appl. No. 09/651,340 Final Office Action mailed Sep. 24, 2002", 10 pgs.

"U.S. Appl. No. 09/651,340 Non Final Office Action mailed May 2, 2002", 15 pgs.

"U.S. Appl. No. 09/651,340 Notice of Allowance mailed Feb. 6, 2003", 5 pgs.

"U.S. Appl. No. 09/651,340 Response filed Aug. 1, 2002 to Non Final Office Action mailed May 2, 2002", 9 pgs.

"U.S. Appl. No. 09/651,340 Response filed Nov. 25, 2002 to Final Office Action mailed Sep. 24, 2002", 8 pgs.

"U.S. Appl. No. 10/431,136 Advisory Action mailed May 25, 2006", 3 pgs.

"U.S. Appl. No. 10/431,136 Final Office Action mailed Mar. 22, 2006", 8 pgs.

"U.S. Appl. No. 10/431,136 Final Office Action mailed Jun. 2, 2004", 14 pgs.

"U.S. Appl. No. 10/431,136 Non Final Office Action mailed Apr. 21, 2005", 8 pgs.

"U.S. Appl. No. 10/431,136 Non Final Office Action mailed Sep. 16, 2005", 11 pgs.

"U.S. Appl. No. 10/431,136 Non Final Office Action mailed Oct. 20, 2004", 11 pgs.

"U.S. Appl. No. 10/431,136 Non Final Office Action mailed Dec. 31, 2003", 10 pgs.

"U.S. Appl. No. 10/431,136 Notice of Allowance mailed Jul. 14, 2006", 4 pgs.

"U.S. Appl. No. 10/431,136 Response filed Jan. 21, 2005 to Non Final Office Action mailed Oct. 20, 2004", 9 pgs.

"U.S. Appl. No. 10/431,136 Response filed Mar. 31, 2004 to Non Final Office Action mailed Dec. 31, 2003", 11 pgs.

"U.S. Appl. No. 10/431,136 Response filed May 18, 2006 to Final Office Action mailed Mar. 22, 2006", 9 pgs.

"U.S. Appl. No. 10/431,136 Response filed Jun. 22, 2006 to Advisory Action mailed May 25, 2006", 6 pgs.

"U.S. Appl. No. 10/431,136 Response filed Jul. 20, 2005 to Non Final Office Action mailed Apr. 21, 2005", 10 pgs.

"U.S. Appl. No. 10/431,136 Response filed Aug. 2, 2004 to Final Office Action mailed Jun. 2, 2004", 10 pgs.

"U.S. Appl. No. 10/431,136 Response filed Dec. 16, 2005 to Non Final Office Action mailed Sep. 16, 2005", 12 pgs.

Tockman, Bruce, et al., "U.S. Appl. No. 11/906,794, filed Oct. 2, 2007", 43 Pages.

* cited by examiner

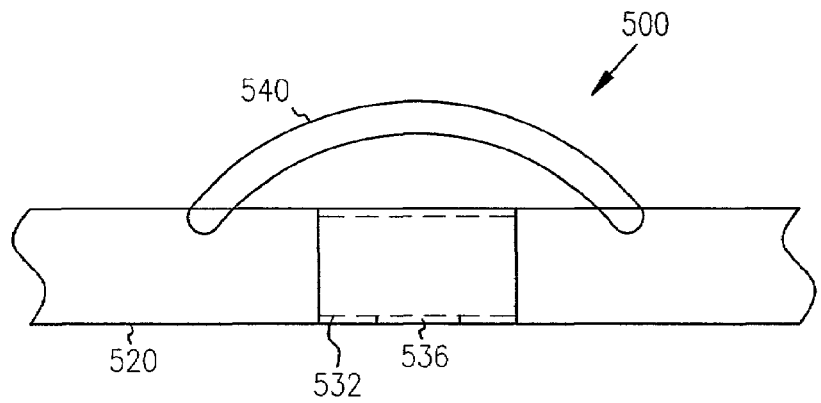
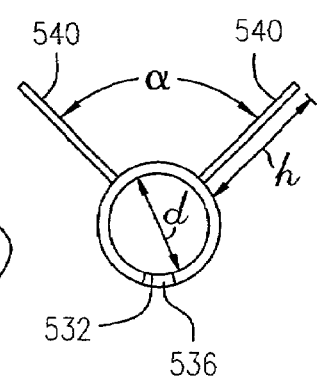
FIG. 5A  FIG. 5B
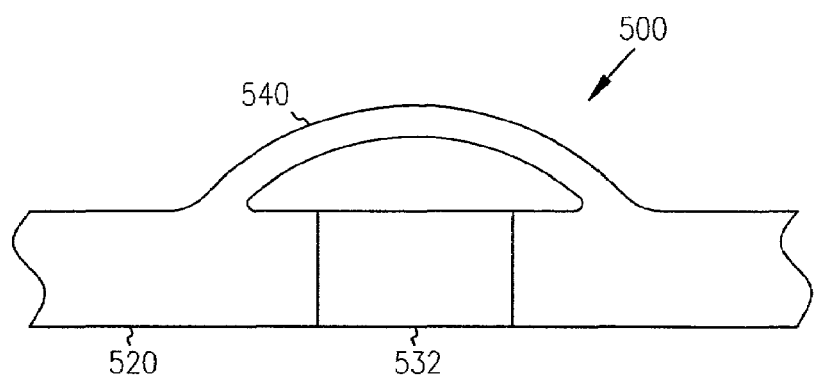
FIG. 5C
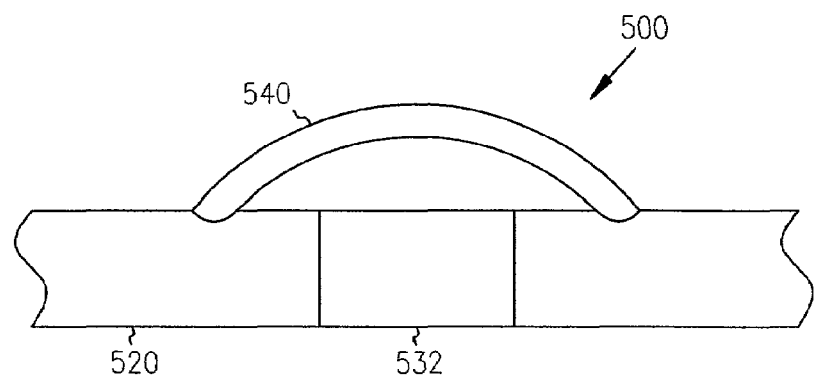
FIG. 5D

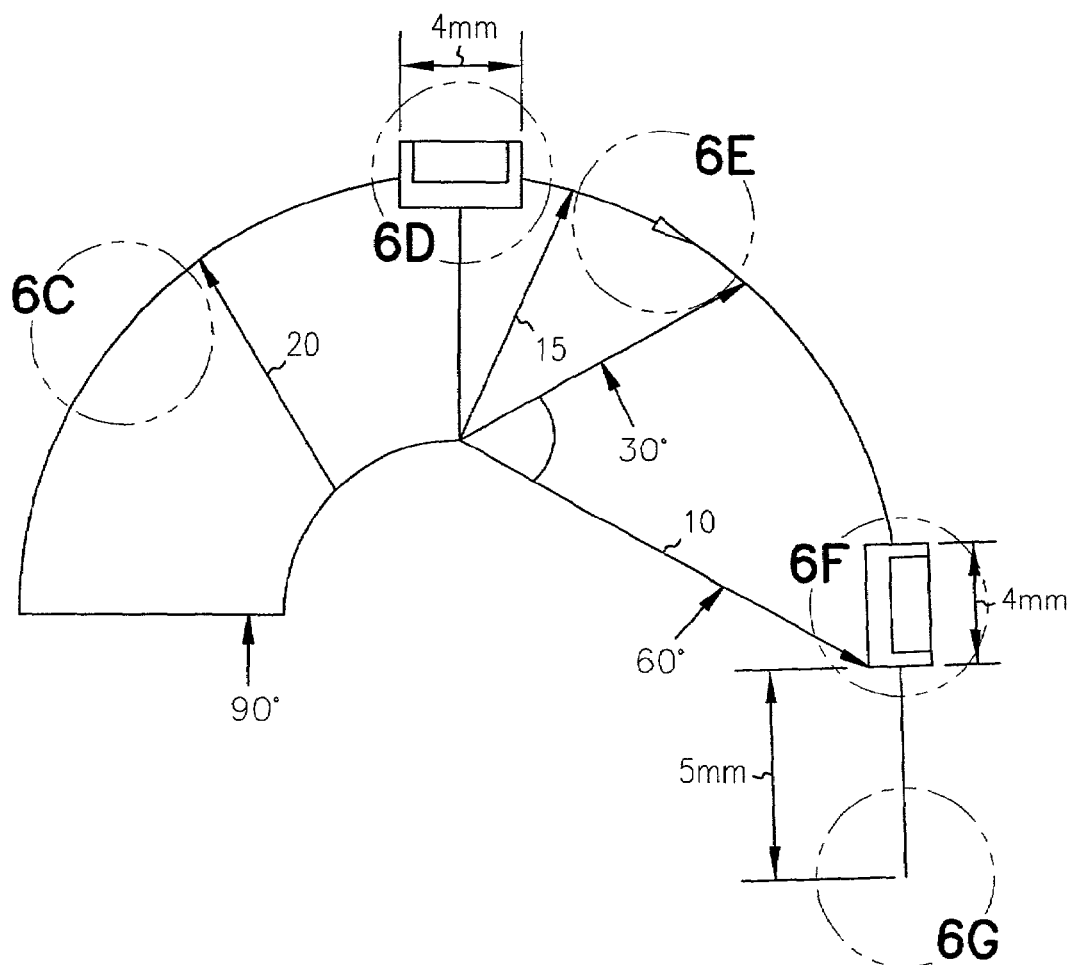
FIG. 6B
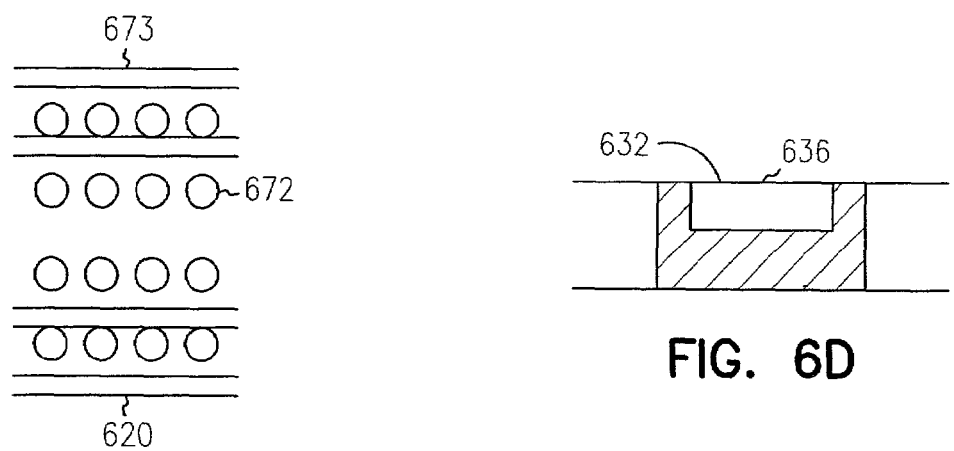
FIG. 6C
FIG. 6D

CORONARY VEIN LEADS HAVING AN ATRAUMATIC TIP AND METHOD THEREFOR

CROSS-REFERENCE TO RELATED APPLICATIONS

This application is a continuation-in-part application to, commonly assigned U.S. patent application Ser. No. 09/651,340, entitled "LEADS FOR PACING AND/OR SENSING THE HEART FROM WITHIN THE CORONARY VEINS" filed on Aug. 30, 2000, now U.S. Pat. No. 6,584,362 the specification of which is incorporated by reference herein in its entirety.

TECHNICAL FIELD

The present subject matter relates to the field of leads for correcting irregularities of the heart. More particularly, this subject matter relates to an atraumatic tip assembly for leads for pacing and/or sensing the heart from the coronary vasculature.

TECHNICAL BACKGROUND

A cardiac pacing system includes a battery powered pulse generator and one or more leads for delivering pulses to the heart. Current pulse generators include electronic circuitry for determining the nature of an irregular rhythm, commonly referred to as arrhythmia, and for timing the delivery of a pulse for a particular purpose. The pulse generator is typically implanted into a subcutaneous pocket made in the wall of the chest. Leads which are attached to the pulse generator are routed subcutaneously from the pocket to the shoulder or neck where the leads enter a major vein, usually the subclavian vein. The leads are then routed into the site of pacing, usually a chamber of the heart. The leads are electrically connected to the pulse generators on one end and are electrically connected to the heart on the other end. Electrodes on the leads provide the electrical connection of the lead to the heart, where the leads deliver the electrical discharges from the pulse generator to the heart.

The electrodes are typically arranged on a lead body in two ways or categories. A pair of electrodes which form a single electrical circuit (i.e., one electrode is positive and one electrode is negative) positioned within the heart is a bipolar arrangement. The bipolar arrangement of electrodes requires two insulated wires positioned within the lead. When one electrode is positioned in or about the heart on a lead and represents one pole and the other electrode representing the other pole is the pulse generator, this arrangement is known as a unipolar arrangement. The unipolar arrangement of electrodes requires one insulated wire positioned within the lead.

Some patients require a pacing system having multiple sites in one chamber of the heart for detecting and correcting an abnormal heartbeat. In the past, a common practice for a patient requiring multi-site pacing within one or more chambers of the heart, would be to provide two separate and different leads attached to the particular chamber of the heart. One lead would be implanted at one site in the chamber. Another lead would be implanted at another site in the same chamber, or another chamber. Typically, the single chamber of the heart receiving multi-site pacing would be the right atrium.

Having two separate leads is undesirable for many reasons. Among these are the complexity of and time required for the implantation procedure for implanting two leads as compared to that of the procedure for implanting one lead. In addition, two leads may mechanically interact with one another after implantation which can result in dislodgement of one or both of the leads. In vivo mechanical interaction of the leads may also cause abrasion of the insulative layer along the lead which can result in electrical failure of one or both of the leads. Another problem is that as more leads are implanted in the heart, the ability to add leads is reduced. If the patient's condition changes over time, the ability to add leads is restricted. Two separate leads also increase the risk of infection and may result in additional health care costs associated with re-implantation and follow-up.

It is well understood that the heart functions with two sides. The right side of the heart receives blood from the body and pumps it into the lungs to exchange gases. The left side of the heart receives the oxygenated blood from the heart and pumps it to the brain and throughout the body. As currently practiced, endocardial pacing and defibrillation leads are positioned within the right chambers of the heart, since the left side pumps blood to the brain. Furthermore, numerous difficulties are encountered when it is desired to sense and pace the left heart endocardially.

Accordingly, there is a need for a endocardial lead that can reliably perform pacing and sensing of the heart without being placed in the left side of the heart.

SUMMARY

A lead assembly includes a lead body adapted to carry electrical signals, where the lead body has a proximal end and a distal end, and an intermediate portion therebetween, and a connector is located at the proximal end of the lead body. At least one conductor is disposed within the lead body, and the lead body has at least one preformed biased portion at an intermediate portion of the lead body. The lead further includes an unbiased, flexible tapered portion disposed between the biased portion and the distal end of the lead body, and the tapered portion distal to the biased portion is substantially more flexible than the biased portion. The lead further includes at least one electrode coupled with at least one conductor.

Several options for the lead are as follows. For instance, in one option, the unbiased, flexible tapered portion terminates at the distal end of the lead body. In another option, the conductor forms an inner lumen therein, and the inner lumen is isodiametric. In another option, none of the conductors extend to the distal end of the lead body, where optionally the conductor terminates within the unbiased, flexible, tapered portion of the lead body. In yet another option, the biased portion has a helical shape, and optionally electrodes are disposed along the helical shape, wherein the electrodes on the helical shape are spaced 120 degrees apart. The lead includes, in another option, radiopaque material molded within material forming the unbiased, flexible, tapered portion.

In another embodiment, a lead assembly includes a lead body adapted to carry signals, such as an open lumen lead, where the lead body extends from a proximal end to a distal end, and has an intermediate portion therebetween. The lead body has at least one preformed biased portion at an intermediate portion of the lead body, and at least one conductor is disposed within the lead body. A flexible portion and, optionally, a tapered portion are included near the distal end of the lead body, where the flexible portion is more flexible than the biased portion. The distal end of the lead body has a tapered portion adapted to be implanted within a passage.

Several options for the lead are as follows, for instance, in one option, the flexible portion extends from the distal tip, or alternatively, from the distal tip to a portion between the bias and the distal tip, or in another option, the flexible portion extends from distal tip to the preformed biased portion. In another option, the tapered portion extends from distal tip to a portion between the preformed biased portion and the distal tip. In yet another option, the flexible portion has a length greater than the tapered portion.

Several other options are also possible. For example, the conductor does not extend to the distal tip, or the biased portion has a helical shape, where electrodes are optionally spaced about 120 degrees apart around the helical shape. In yet another option, the distal end of the lead body includes a premolded tip assembly filled with radiopaque material.

In another embodiment, a method includes placing a guidewire within one or more passageways of a body, and threading a lead assembly over the guidewire. The lead assembly includes a lead body adapted to carry signals, where the lead body has a proximal end and a distal end, and an intermediate portion therebetween. The lead assembly further includes a connector located at the proximal end of the lead body, and at least one conductor is disposed within the lead body. The lead body has at least one preformed biased portion at an intermediate portion of the lead body, and a flexible portion and a tapered portion are disposed between the biased portion and the distal end of the lead body. The tapered portion is distal to the biased portion and is more flexible than the biased portion. The method further includes biasing one or more electrodes against a wall of at least one of the passageways, and placing the distal end in a cardiac vein.

Several options for the method are as follows. For instance, in one option, the method further includes viewing the distal tip assembly under fluoroscopy, where the lead assembly includes a distal tip assembly including a premolded portion filled with radiopaque material. In another option, the method further includes flexing the distal end of the lead body. Optionally, biasing the electrodes against the wall of the passageway includes positioning one or more electrodes around a helical portion of the lead body.

The above described leads advantageously provide the ability to sense and pace the heart using leads positioned within the cardiac vasculature, and further the leads provide the ability to pace and/or sense the left heart. It has been found that by placing a therapeutic lead near the atrium, but not in the atrium, higher amplitude electrograms may be detected as compared to a standard endocardial lead. Further, it has been found that left sided pacing may help suppress atrial arrhythmias, particularly those originating near the left atrium. Still further, it has been found that the ability to critically control the timing between pacing the atria and ventricles of the heart is of utility in optimizing pacing therapies.

The leads described herein involve geometries that facilitate positioning the lead assembly within the vasculature, and further help insure that an optimally positioned lead will remain in that position well beyond the time of implant. The lead designs discussed herein yield reliable and optimal performance in sensing and pacing of the heart.

The lead advantageously allows for effective use of a biased portion on a lead body in combination with an atraumatic tip assembly. The biased portion allows for gentle and effective forces against passage walls enabling the lead to be positionally maintained therein. In addition, the biased portion ensures the electrode is placed up against the passage wall with sufficient force. The spacing of the electrodes along the biased portion provides for an increased opportunity for the electrode to be placed against the passage wall. The atraumatic tip assembly is extremely flexible, relative to the biased portion, which allows for improved maneuverability of the lead through tortuous vasculature, and allows for the lead to be implanted more easily and quickly than conventional leads. Furthermore, the flexible tapered portion of the atraumatic tip assembly allows for the guidewire or stylet, if used, to better guide the lead without interference from the biased portion.

These and other embodiments, aspects, advantages, and features of the present invention will be set forth in part in the description which follows, and in part will become apparent to those skilled in the art by reference to the following description of the invention and referenced drawings or by practice of the invention. The aspects, advantages, and features of the invention are realized and attained by means of the instrumentalities, procedures, and combinations particularly pointed out in the appended claims and their equivalents.

BRIEF DESCRIPTION OF THE FIGURES

FIG. 5A is a side view of a portion of a coronary vein lead constructed in accordance with one embodiment;

FIG. 5B is an end view of a coronary vein lead constructed in accordance with one embodiment;

FIG. 5C is a side view of a portion of a coronary vein lead constructed in accordance with one embodiment;

FIG. 5D is a side view of a portion of a coronary vein lead constructed in accordance with one embodiment;

FIG. 6B is a side view of a coronary vein lead constructed in accordance with one embodiment;

FIG. 6C is an enlarged cross section of a portion of the lead as shown in FIG. 6B;

FIG. 6D is an enlarged cross section of a portion of the lead as shown in FIG. 6B;

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

Figure 1A:
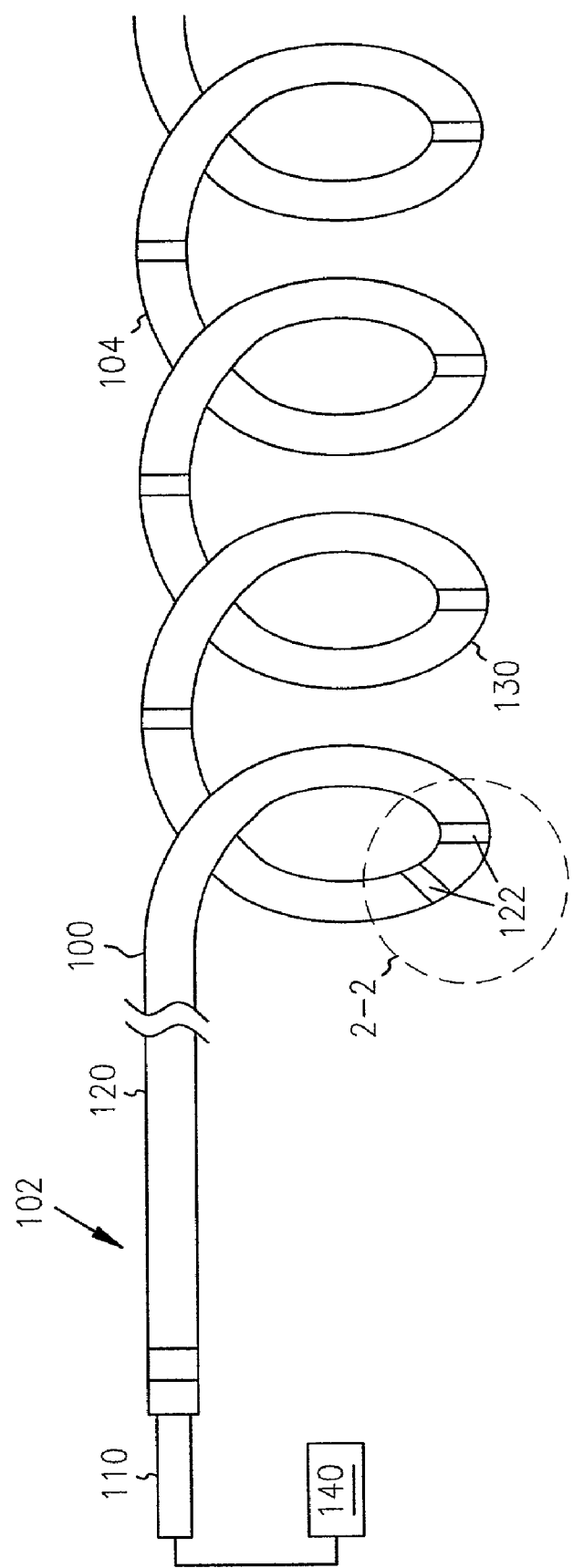
FIG. 1A is a side view of a coronary vein lead constructed in accordance with one embodiment.

FIG. 1A is a side view of one example of a coronary vein lead 100. The lead 100 has a proximal end 102 and a distal end 104 and includes a connector terminal 110 and a lead body 120. The lead 100 attaches to a pulse sensor and generator 140. In one embodiment, the lead 100 is constructed and arranged for insertion into the coronary sinus, as discussed further below. The lead body 120 has a number of electrodes 122 in its distal end 104 which is implanted in a coronary vein. The connector terminal 110 electrically connects the various electrodes and conductors within the lead body 120 to a pulse sensor and generator 140. The pulse sensor and generator 140 contains electronics to sense various pulses of the heart and also produce pulsing signals for delivery to the heart. The pulse sensor and generator 140 also contains electronics and software necessary to detect certain types of arrhythmias and to correct for them.

The lead 100, in one option, operates similarly to a bipolar lead having positive and negative portions of a circuit located in the lead body 120. It should be noted that this lead may also be made a unipolar lead. In other words, one electrode or both electrodes of the lead body 120 can be pacing/sensing electrodes, or one electrode can be a pacing/sensing electrode and the anode can be the pulse generator.

The lead body 120, in one option, is a tubing material formed from a polymer biocompatible for implantation, and preferably the tubing is made from a silicone rubber polymer. Alternatively, the lead body 120 may be made of a biocompatible material having shape memory characteristics such that it will return to its preformed shape once implanted and a stylet or guidewire is removed. An example of such a material is polyether polyurethane. In addition, the lead body 120 optionally has portions which have shape memory characteristics, comprising either a shape memory polymer or a shape memory metal. The lead body contains several electrical conductors. The electrical conductors are made of a highly conductive, highly corrosion-resistant material. The electrical conductors carry current and signals between the pulse sensor and generator 140 and the electrodes located at the distal end 104 of the lead 100. Electrical conductors are shown, for example, at 472 and 473 of FIGS. 4B and 4C, and at 672 and 673 of FIGS. 6C, 6E and 6G.

Figure 1B:
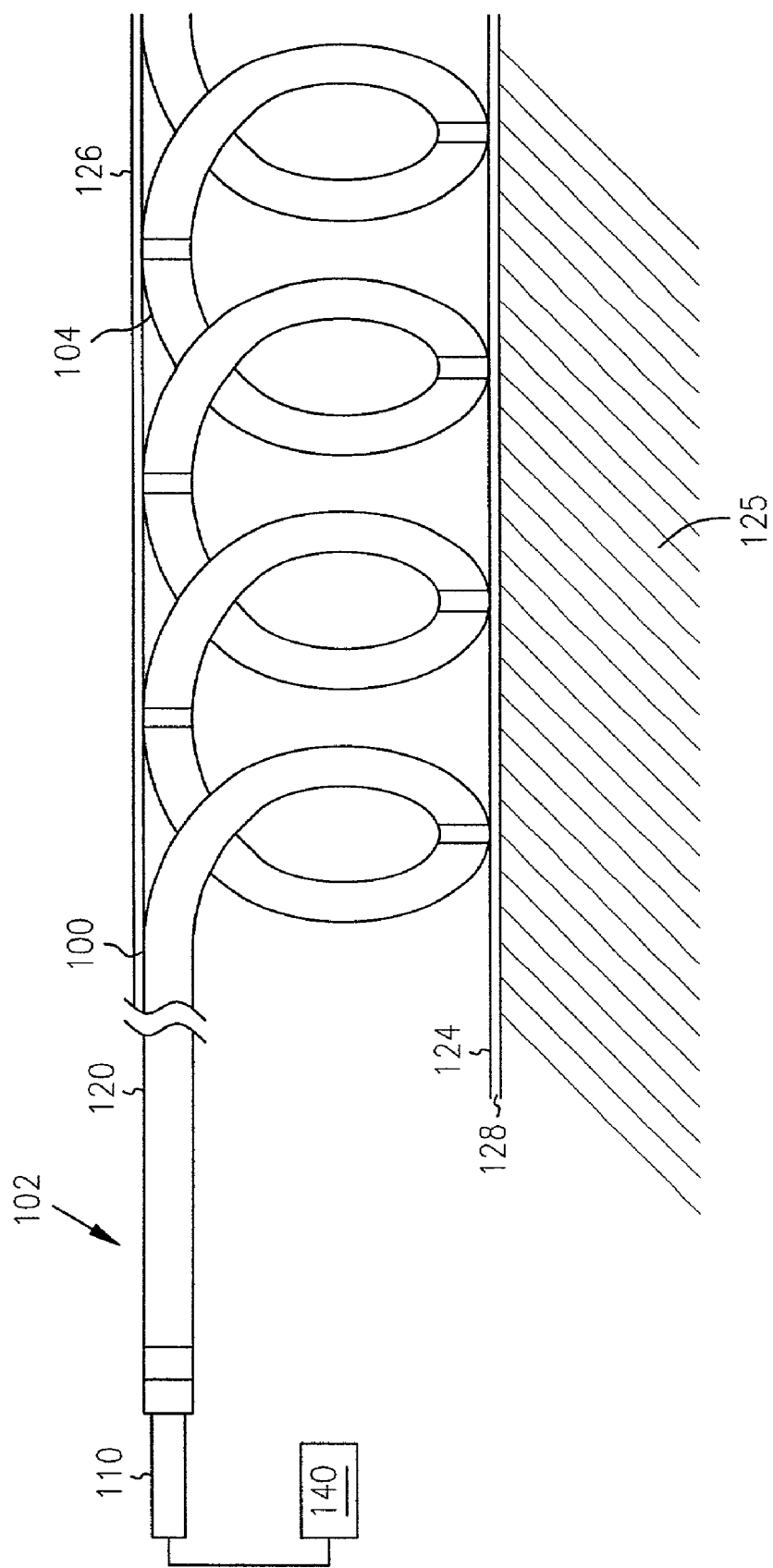
FIG. 1B is a side view of a coronary vein lead constructed in accordance with another embodiment.

The lead body 120 optionally has a helical portion 130 near the distal end 104. The helical portion 130 includes a three-dimensional bias adapted to bias at least a portion of the lead body 120 or electrode against a wall of a passage, as further discussed below. After implantation into a patient, in one option, the helical portion 130 will be located in a coronary vein, as shown, for example, in FIG. 1B. Referring to FIG. 1B, a coronary vein 124 is shown which includes a free wall 126 and a myocardial wall 128. The free wall 126 is faced away from an inner portion of the heart 125, and the myocardial wall 128 abuts the inner portion of the heart 125.

The helical portion 130 of the lead body 120 is optionally made of a biocompatible material having shape memory characteristics such that it will return to its preformed helical shape once implanted and a stylet or guidewire is removed. An example of such a material is polyether polyurethane. In addition, the lead body may have portions which have shape memory characteristics, comprising either a shape memory polymer or a shape memory metal. The diameter of the helical shape is, in one option, about 0.25 cm-2 cm. The pitch of the helix, in one option, ranges from 0.5 cm-2.5 cm. It should be noted that the helical shape can be formed by any number of turns, including, but not limited to, multiple turns, a single turn, or less than one turn.

As mentioned above, the helical portion 130 includes electrodes 122. In one option, the electrodes 122 are evenly spaced at about 120 degrees apart, which increases the opportunity for the electrodes 122 to make contact with the myocardial wall 128. In a further option, pairs of electrodes 122 are evenly spaced about 120 degrees apart along the lead body 120. The electrodes 122 are electrically coupled with one conductor, or are electrically coupled with separate conductors.

The helical portion 130 of the lead body 120 facilitates placement of the electrodes against the myocardial wall 128 of the coronary vein 124 during and/or after implantation. The helical shape of the lead 100 provides large lead/vessel wall area interface to produce reliable, long term stability. When implanted, the helical shape of the lead 100 produces subtle lateral forces between the electrodes 122 and myocardial wall 128, resulting in low pacing thresholds.

Figure 2:
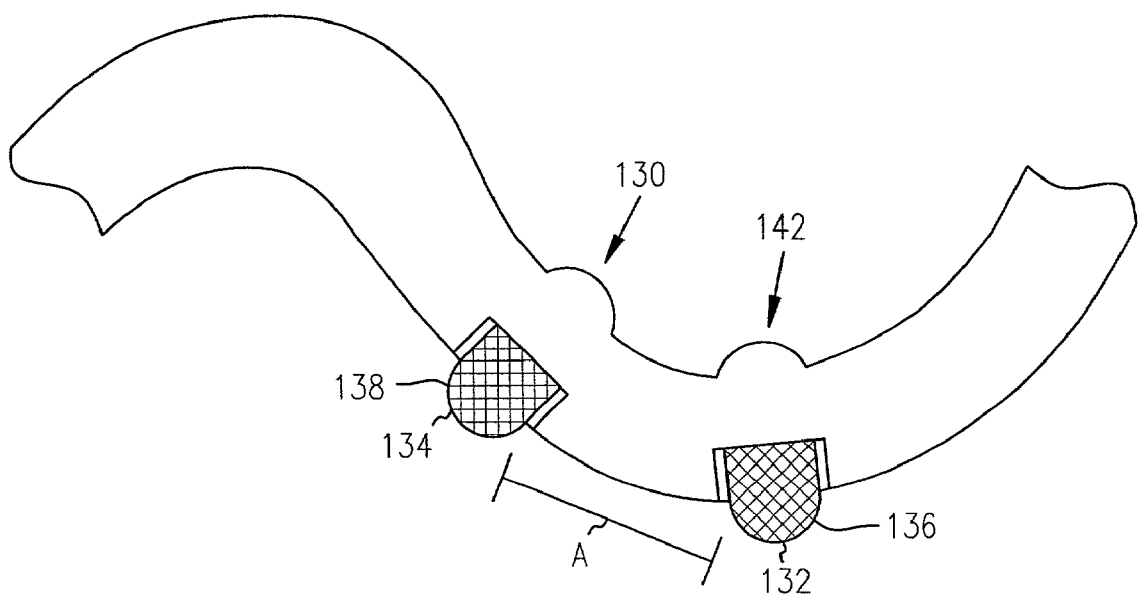
FIG. 2 is an enlarged view of the lead of FIG. 1A, taken along circle 2-2 of FIG. 1.

Referring to FIGS. 1A and 2, the distal end 104 of the lead 100 includes several electrodes 122, and in one example has two electrodes 132, 134. The first electrode 132 is generally referred to as the distal electrode. A second electrode 134 is located near the distal electrode and proximally thereof and can be used as a counter electrode for electrode 132 or for defibrillation therapy. The lead 100 maybe generally described as a tachycardia (tachy) lead, although it is not limited thereto. The electrodes 132, 134 are of an electrically conductive material such as an alloy of platinum and iridium which is highly conductive and highly resistant to corrosion. The electrodes 132, 134 optionally include a passive fixation portion. Electrodes 132 and 134 are masked or otherwise insulated on the inside radius 142 of the distal end 104 of the lead 100. This decreases electrode area and provides desired increase in impedance. The bipolar electrode pair spacing between electrodes 132 and 134 is shown at line A of FIG. 2 to be from about 1-5 mm. With such close electrode spacing, increased rejection of problematic far field (ventricular) signals is accomplished. Optionally, the electrode surfaces 136, 138 are raised beyond the body 120 of the lead 100. Electrodes designed in this fashion increase the chances of achieving intimate tissue-electrode contact thereby resulting in lower thresholds.

Figure 3A:
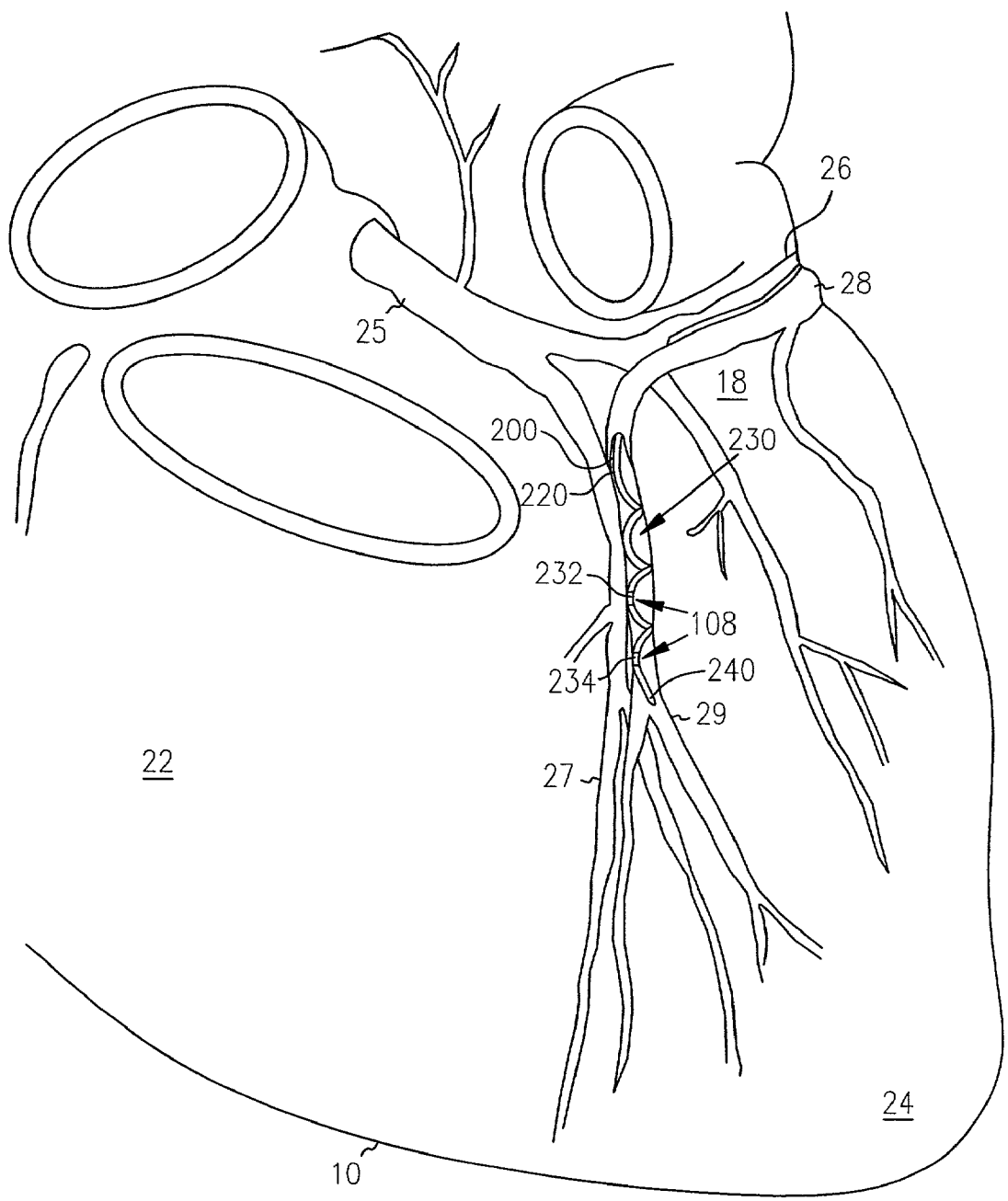
FIG. 3A is side view of a coronary vein lead constructed in accordance with one embodiment, shown positioned in a coronary vein.

FIG. 3A shows an alternative embodiment of a coronary vein lead 200 which has a helical distal end 230, where the heart 10, left ventricle 22, right ventricle and apex 24 of the heart 10 are shown. It should be noted that the helical distal end 230 includes any of the above discussed helical configurations, and can be combined with any of the embodiments discussed below. The left coronary artery 25 branches into the circumflex artery 26 and the anterior descending artery 27. The coronary sinus 28 branches into the coronary branch vein 29. Placing the lead 200 in the coronary branch veins, for example, on the left ventricle has been found to be a suitable means for delivering pacing therapy to patients suffering from congestive heart failure, without having to position the lead 200 within the left ventricle.

Figure 3B:
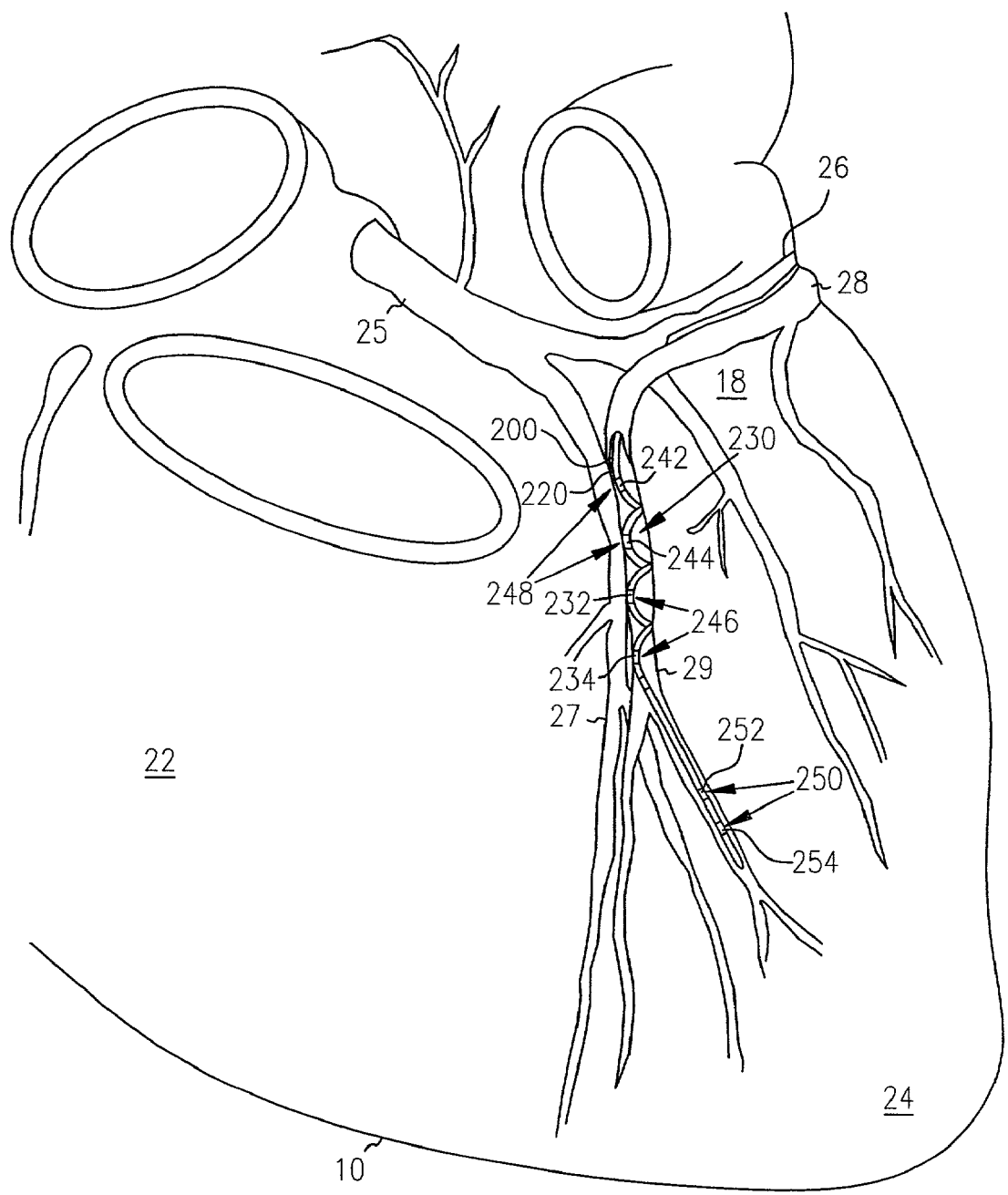
FIG. 3B is side view of a coronary vein lead constructed in accordance with another embodiment, shown positioned in a coronary vein.

Referring to FIG. 3B, the lead 200 is adapted to be used within the coronary artery 25 and also within the coronary branch vein 29. A coronary vein lead 200 with a helical distal end 230 is shown located in an implanted site. The coronary vein lead 200 includes a mid ventricular electrode pair 246 (electrodes 232 and 234). The electrodes 232, 234 are shown in intimate contact with the vessel wall 108 of the branch vein 29, where the electrodes 232, 234 contact the myocardial wall, as discussed above. The coronary vein lead 200 optionally includes a mid ventricular electrode pair 246 (electrodes 232 and 234) and further optionally includes an apical electrode pair 250 (electrodes 252 and 254). The helical portion 230 and the spacing of the electrodes positions the electrodes 232, 234 against the myocardium to reduce pacing thresholds. The helix diameter is such that a vein of any size will reduce the diameter of the helix so that at least one electrode will be pressed against the myocardial wall. The lead 200 optionally has a fixation mechanism 240, as shown in FIGS. 3A and 3C.

In one embodiment shown at FIG. 3B, multiple smaller electrodes 232, 234, 242, 244 are strategically placed along the helix 230 thereby increasing the probability of direct electrode contact on the myocardial wall of the vein versus the free wall. For example, multiple electrodes are spaced apart along the helix 230 to span from the apex 24 to the base 18 of the heart 10. Electrodes 232, 234 form a midventricular electrode pair 246 and electrodes 242, 244 form a basal electrode pair 248, so designated by their proximity to a particular region of the heart when the lead 200 is in its implanted site in the heart 10. In one embodiment, lead 200 has an apical electrode pair 250 formed of electrodes 252, 254 which have a proximity to the apex 24 of the heart 10 when implanted. The portion of the lead 200 including the apical electrode pair 250 optionally includes a helical portion. In another option, instead of pairs, single electrodes, or more than two electrodes can be included in that discussed above.

In an embodiment where multiple electrodes are connected to the same conductor, the electrode with the best tissue contact will serve as the stimulating electrode. In one embodiment, the lead 200 has multiple electrodes and conductors, and the electrodes which are the cathodes or anodes are selected depending on the thresholds acquired at each stimulation site. As an example, in a bipolar lead, optimal therapy may be achieved by choosing the tip or ring (such as are shown, for example, at 750 and 734 of FIG. 7) as cathode or anode depending on the different thresholds. In the embodiments shown at FIGS. 3A and 3B, multiple electrode capacity is provided in the left ventricular vein. These electrodes are capable of pacing together, or alternatively with only a pair of the electrodes pacing together. Further, the electrodes optionally pace with a delay between them or sequentially.

Figure 3C:
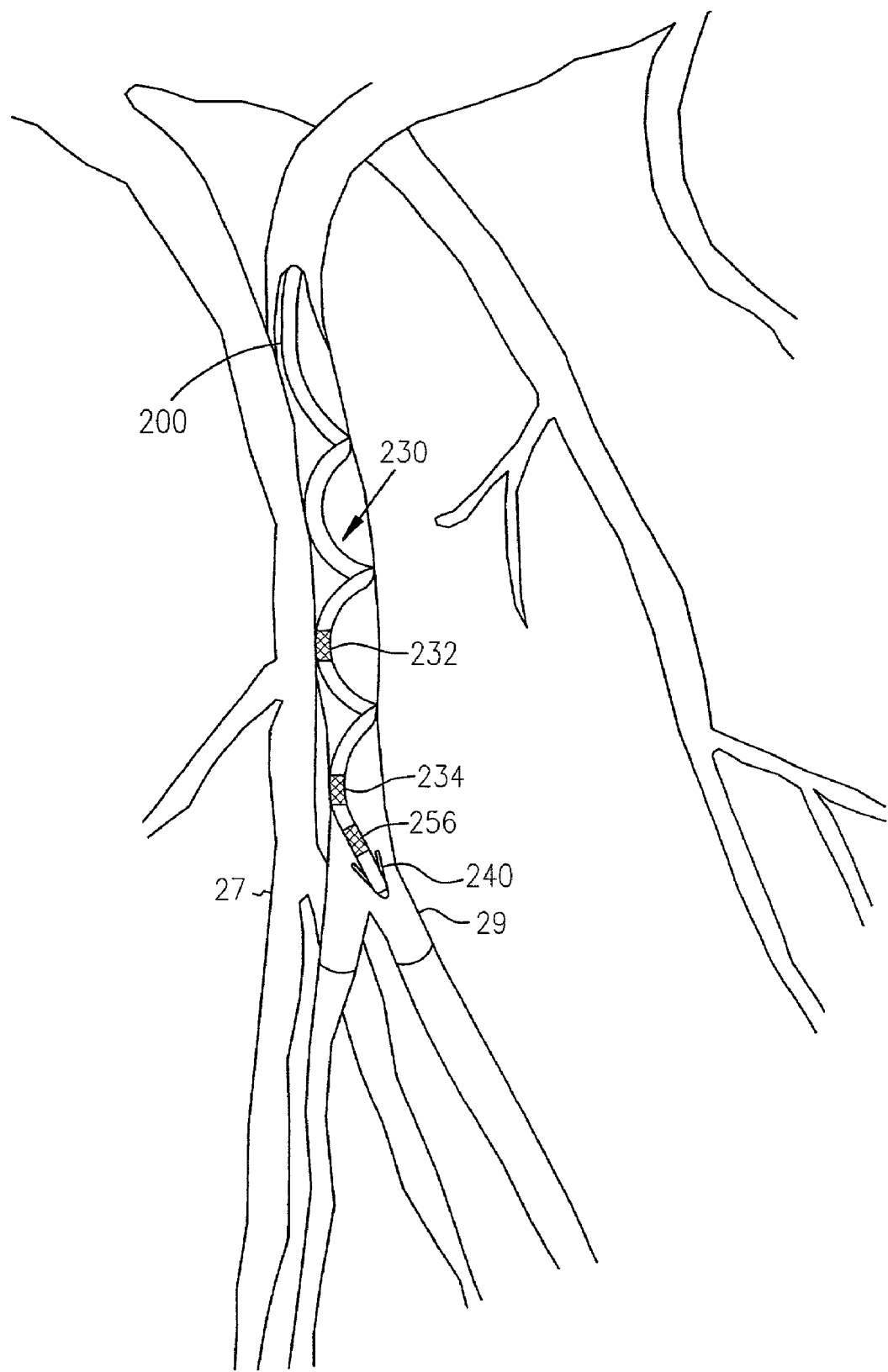
FIG. 3C is side view of a coronary vein lead constructed in accordance with another embodiment, shown positioned in a coronary vein.

Referring to FIG. 3C, a steroid is optionally used to ensure pacing at the cathodal site. The steroid is located in close proximity of the cathode electrode, for example, electrode 234, and not in close proximity of the anode electrode. The steroid is provided by way of steroid collar 256 loaded with the desired drug which is then time released. The steroid collar 256 is external to the lead body 220, and adjacent to the electrode. The drug has a very localized effect, thereby requiring close proximity to the cathode. Steroid release in close proximity to the anode electrode is not critical, but may be allowed. This placement of the steroid collar 256 ensures that the cathode electrode paces first, and before the anode electrode. An example of such a drug is dexamethasone acetate. In another option, a steroid collar or a steroid coating, for example, is provided as a generally cylindrical component adjacent one or both sides of an electrode of any lead described herein.

Another option for the leads described herein involves the use of local drug elution, for example a steroid, in the vicinity of the electrodes. In many applications, desired low chronic pacing thresholds can be achieved through the local release of at least one pharmacologically active agent. This can be easily accomplished by compounding agents into polymeric components positioned adjacent to the electrodes. A pharmaceutical agent typically used in pacing applications is one possessing anti-inflammatory action. Dexamethasone, dexamethasone sodium phosphate and dexamethasone acetate have been used in commercially released devices. Other agents with other actions are other options. For example, steroidal anti-inflammatory agents other than dexamethasone, nonsteriod anti-inflammatory agents, as well as antiarrhythmic, antibiotic, anticoagulative, thrombolytic and other agents known to improve biocompatibility and/or electrical therapies are optionally used.

For steroid release to be therapeutic, it must occur in very close proximity to the electrode. As such, in one embodiment, the steroid is released from the interior of an electrode and subsequently delivered directly to the heart tissue contacting the electrode. This is accomplished by first compounding a biocompatible polymer (such as silicone) with a steroid substance (such as dexamethasone) and then molding the polymer-drug matrix into a small component than can finally be positioned within a porous electrode. Alternatively, a polymer-drug matrix is molded into a generally cylindrical component that can be subsequently positioned adjacent to one or both sides of a generally cylindrical electrode. Another alternative is to apply a thin coating of the polymer-drug matrix to the completed lead body construction in locations consistent with the needed close proximity to the electrode. In yet another option, a steroid collar is used, as discussed above.

Figure 4A:
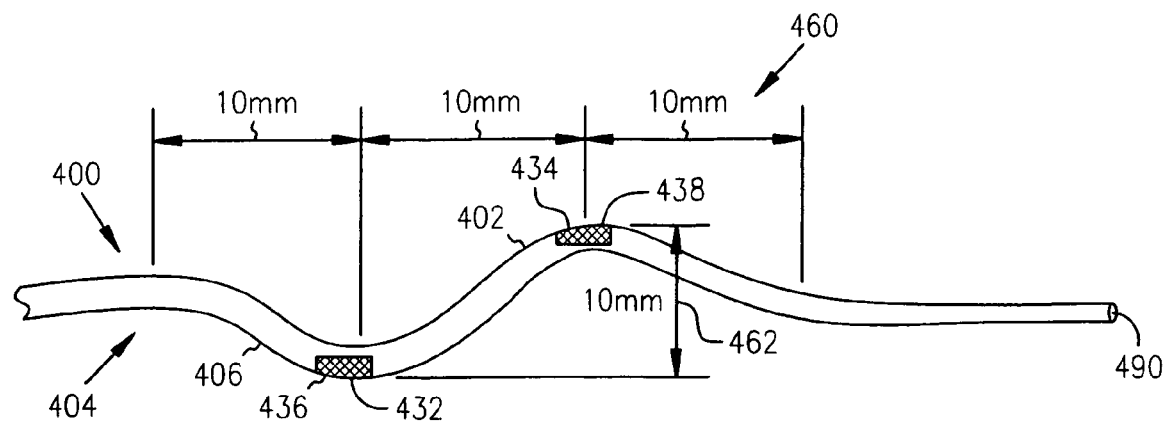
FIG. 4A is a side view of a coronary vein lead constructed in accordance with one embodiment.

In one embodiment, the lead is constructed and arranged for fixation in the coronary sinus. For example, the lead has specific biases to facilitate placement and retention in passageways such as the coronary sinus. Referring now to FIG. 4A, a double-bias lead 400 constructed and arranged for fixation in the coronary sinus is shown. It should be noted that the double-bias lead 400 can be combined with embodiments discussed above and below. The lead 400 includes a first bias 402 and a second bias 406, although an additional bias is optionally further provided with the lead 400. The first bias 402 is disposed in a direction that is different than the second bias 406, and in one option, the biases 402, 406 lie in the same plane (i.e. 2-dimensions).

Figure 4B:
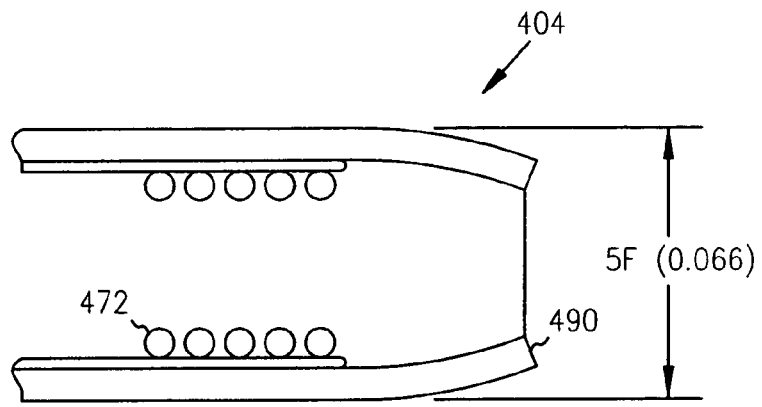
FIG. 4B is a side view of a coronary vein lead constructed in accordance with one embodiment.
Figure 4C:
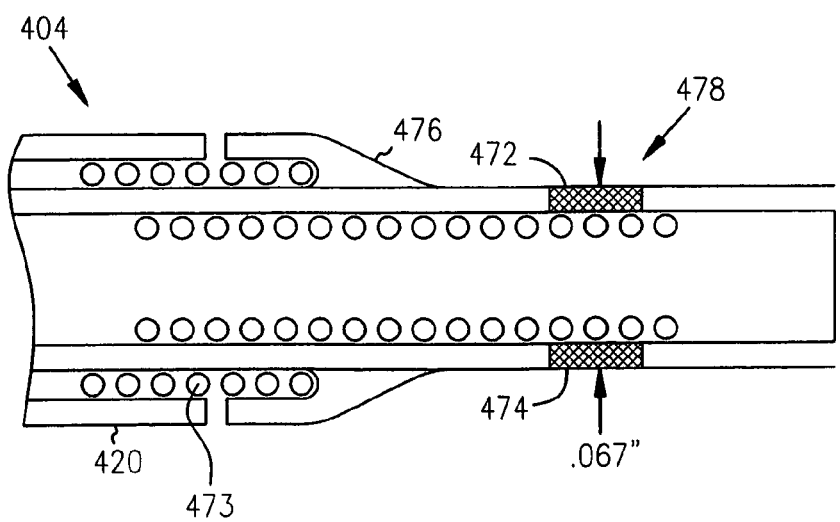
FIG. 4C is a side view of a coronary vein lead constructed in accordance with one embodiment.

At FIG. 4A, a lead 400 is shown including half ring electrodes 432, 434 which are biased against the vessel wall by a biased portion 460 of the lead 400. In one embodiment, the electrodes 432, 434 are spaced about 10 mm apart along the lead 400, and the length of the biased portion 460 is about 30 mm. In one embodiment, the lead 400 is constructed and arranged so a first plane including a surface 438 of the electrode 434 is spaced about 10 mm from a second plane including a surface 436 of the electrode 432. The lead 400 in one embodiment is an over the wire lead with an open distal end, as shown in FIG. 4B. A distal portion 404 near distal end 490 has a diameter of about 0.066 inch (5 French).

Figure 4D:
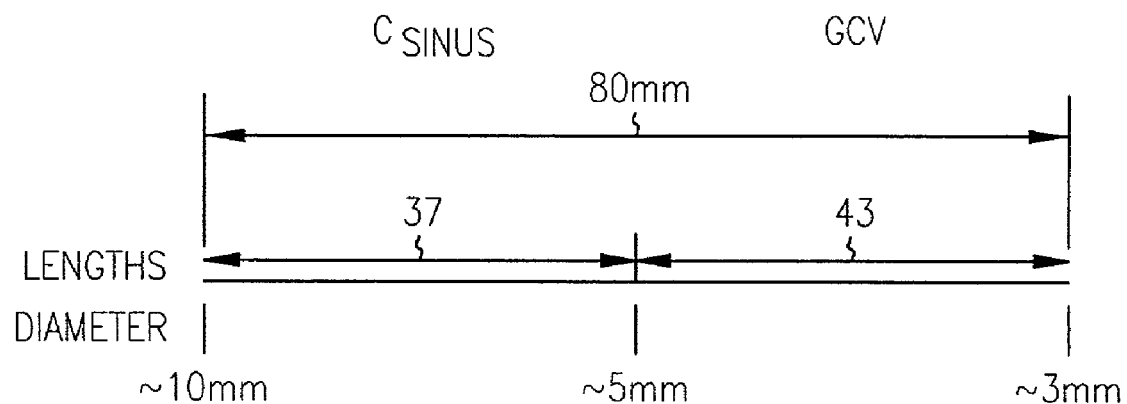
FIG. 4D shows lengths and diameters of a coronary vein lead constructed in accordance with one embodiment.
Figure 4E:
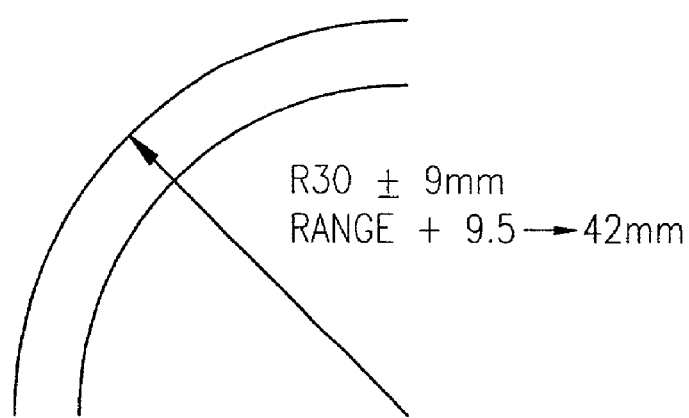
FIG. 4E shows radii of a coronary vein lead constructed in accordance with one embodiment.

The lead 400, in one option, has a length which fits within the coronary sinus/great cardiac vein. The bias portion 460 pushes the electrode up against the vein wall. The bias portion 460 is constructed and arranged to fit within the area of the coronary sinus/great cardiac vein around the mitral valve. The lengths and diameters of the coronary sinus/great cardiac vein are shown at FIG. 4D. The coronary sinus has a length of about 37 mm and the great cardiac vein has a length of about 43 mm, for a combined length of about 80 mm. The diameter of the proximal end of the coronary sinus at the thebesian valve is about 10 mm. Where the coronary sinus and the great cardiac vein meet at the distal end of the coronary sinus and the proximal end of the great cardiac vein at the valve of vieussens, the diameter is about 5 mm. The distal portion of the great cardiac vein has a diameter of about 3 mm.

The mitral valve may have a radius (R) between about 9.5 mm-42 mm. In general the radius is about 30 mm. In one embodiment, the biased lead portion 460 shown at FIG. 4A has a radius between about 9.5 mm to about 42 mm. In one embodiment, the biased portion has a radius of about 30 mm. The biased portion 460 of lead 400 urges electrodes 432,434 against the vein wall. The diameter of the bias portion 460 of lead 400 is between electrodes 432 and 434, in one option, is larger than the diameter of the vein to provide a snug fit. In one embodiment the diameter is about 10 mm. Subtle lateral forces on vessel wall produce reliable long term stability. Lateral forces between electrode and vessel wall result in low pacing thresholds. In one embodiment, the distal end of the lead 400 has a diameter of about 0.066".

Referring to FIG. 4B, in one embodiment the lead 400 has an atraumatic tip 490 having an outer diameter of about 5 French (0.066 inch) and an inner diameter of about 0.038 inch. The interior space between coils 472 has a diameter of about 0.018 inch. Atraumatic tip 490 in one embodiment comprises silastic tubing extending beyond the coils 472 to avoid bruising the vasculature during implantation therein. At FIG. 4C the transition 476 from a portion of lead body 420 which has two coils to the distal portion having one coil 478 is shown. In one embodiment, the distal portion having one coil 478 has an outer diameter of about 0.066 inch. In one embodiment the distal portion 404 has a ring electrode 474. In one embodiment the lead has an outer diameter of about 0.067 inch at the point where electrode 474 is located.

Because the lead 400 of FIG. 4A is designed to be implanted inside the coronary sinus/great cardiac veins (CS/GCV), the size of the lead in relation to the veins is very important. The leads described herein are designed to be held in place by wall tension, i.e. by the force of the lead against the heart wall. The lead 400 must be small enough to slide into place and not damage the walls by excess forces. The lead bias or holding mechanism must not be too small or the lead 400 may become dislodged and fall out. The biased portion 460 must not be too long or it will extend into the atrium. Referring to FIG. 4D, the length of the coronary sinus and great cardiac veins together is 80 mm. If the pacing electrodes are desired to sit in the middle of that vein when the tip 490 of the lead 400 is located at the end of the great cardiac veins, the electrode should be placed about 43 mm proximal to the tip. The diameter of the vein averages at 10 mm at the os (entrance) and goes down to an average of 3 mm at the end of the great cardiac veins. As such, the intended position in the implanted site, or the final lead position, is considered in the lead design so that in its final position the lead 400 is wedged or held in the appropriate place. The outer diameter of the portion that is being wedged in place would be about 20 to 30% larger than the inner diameter of the blood vessel. For example, referring to FIG. 4A, the dimension 462 of the biased portion 460 is 10 mm. This would wedge into a portion of the vein that is about 7 mm in diameter, which is near the end of the coronary sinus near the beginning of the great cardiac veins.

In one embodiment, the lead body 420 may be made of a biocompatible material having shape memory characteristics such that it will return to its preformed shape once implanted and a stylet or guidewire is removed. An example of such a material is polyether polyurethane. In addition, the lead body may have portions which have shape memory characteristics, comprising either a shape memory polymer or a shape memory metal.

FIGS. 5A-5D show a lead 500 constructed and arranged for fixation in the coronary sinus, where the lead 500 includes any of the above and below discussed leads. The silicone arches 540, in one option, are attached to and extend from a lead body 520 opposite the contact area 536 of electrode 532. The arches 540 provide spring forces to position the electrode 532 against the vessel wall, and help to reduce dislodgement and keep pacing thresholds lower. The arches 540 also reduce complications arising in the event that the lead 500 must be removed. Referring to FIG. 5C, in one option, the arch or arches 540 are part of a molded part of the lead 500. In another option, as shown at FIG. 5D, the arches 540 are straight silicone rubber cylinders affixed to the lead body 520 wall by glue in two locations that force the cylinders to assume an arched configuration. Alternatively, molded components in the shape of an arch are positioned on the lead body 520, as shown at FIGS. 5A and 5B.

The arches 540, in one option, straddle the electrode 532, as shown in FIGS. 5A, 5C, and 5D. In operation, any of the above mentioned arches 540 provide a side thrust to the lead body 520 when that lead body 520 is advanced into a narrow vessel with an inner diameter less than the combined distance of the lead body outer diameter (d, as shown at FIG. 5B) and the maximum height (h, as shown at FIG. 5B) of the arch. The side thrust will force the electrode 532 against the vessel wall in a position opposite of the arches 540. These arches 540 are provided to reduce the rate of two types of complications. First, during implantation of a lead body 520 having arches 540, that lead body 520 could be manipulated back and forth in the vessel. Second, and consistent with the first advantage, repositioning or removal of a subchronic or chronic lead will be easier than if the lead had free ended springs (like tines) entangling tissues when manipulation in at least one direction is needed. In an alternative embodiment, the lead 500 also comprises a helical portion as shown at FIGS. 1-2 and 3A-3C. In one embodiment, the lead body 520 may be made of a biocompatible material having shape memory characteristics such that it will return to its preformed shape once implanted and a stylet or guidewire is removed. An example of such a material is polyether polyurethane. In addition, the lead body may have portions which have shape memory characteristics, comprising either a shape memory polymer or a shape memory metal.

Figure 6A:
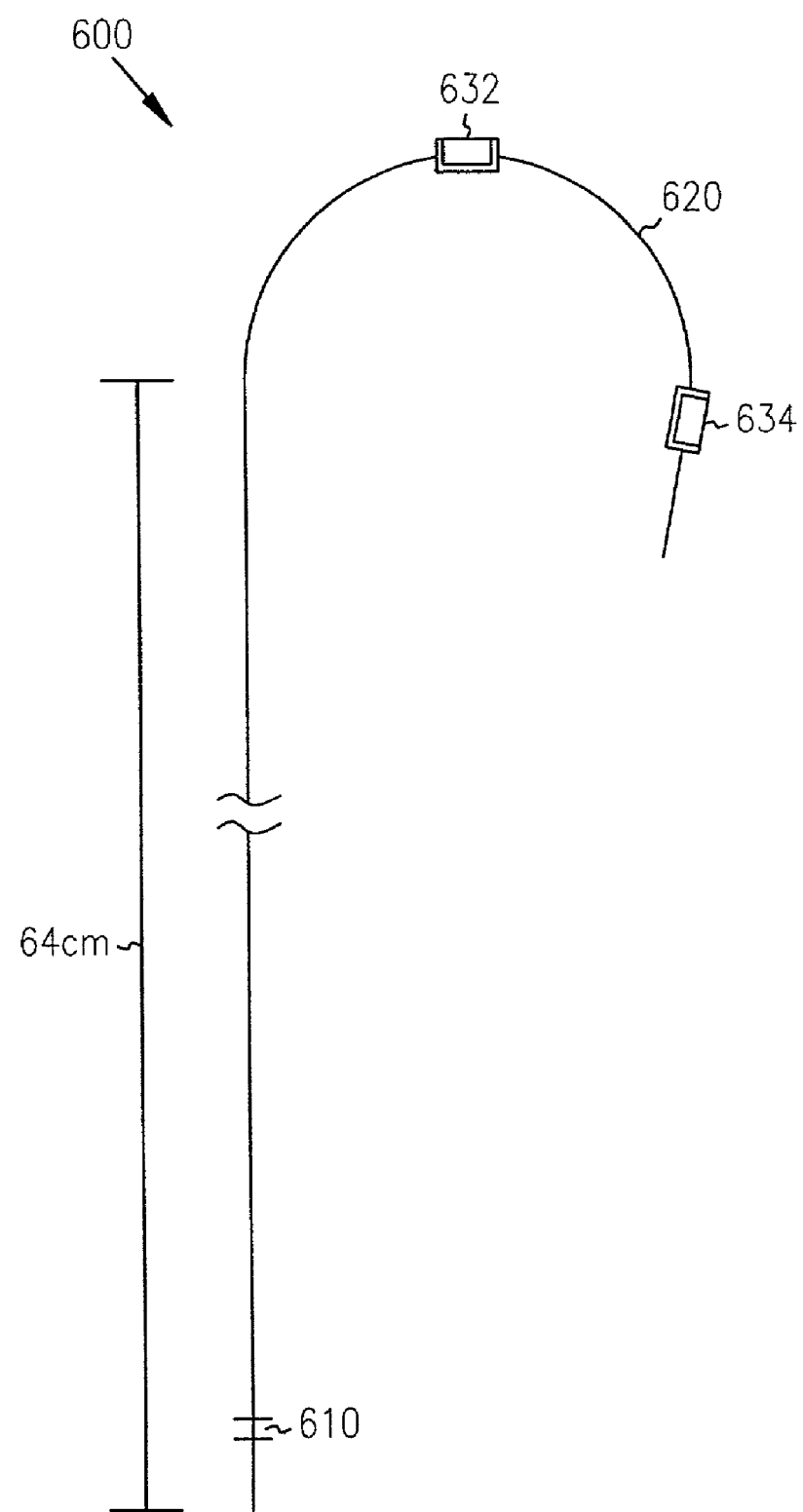
FIG. 6A is a side view of a coronary vein lead constructed in accordance with one embodiment.

FIGS. 6A-6G show a lead 600 adapted for implantation and fixation in the coronary sinus. It should be noted that lead 600, as well as the other embodiments discussed above and below, are, in one option, chronically implanted. FIG. 6A shows the entire lead 600, and FIGS. 6B-6G illustrate a portion of the lead 600. The lead body 620 is generally shaped with the same or smaller radius of curvature as the coronary sinus, so that it hugs the anatomy of the coronary sinus when the lead 600 is implanted. The shape of the lead body 620 hugging the myocardial wall of the coronary sinus urges the electrodes 632, 634 against the wall of the coronary sinus. Because of this geometry compatibility, the lead 600 will have good long term stability with relatively small forces on the lead body 620 and vessel walls. By distributing forces along the extent of the lead body 620, the possibility of lead or vessel wall damage is reduced. FIG. 6B shows the distal portion of one embodiment of lead 600 in greater detail.

The radii of curvature and angles along different portions of the lead body are shown. In one option, the lead body 620 is made of a biocompatible material having shape memory characteristics such that it will return to its preformed shape once implanted and a stylet or guidewire is removed. An example of such a material is polyether polyurethane. In addition, the lead body may have portions which have shape memory characteristics, comprising either a shape memory polymer or a shape memory metal. In another option, the lead body 620 is preformed such that is has a shape adapted to hug the heart while the lead 600 is disposed in the coronary sinus. It should be noted that the hugging shape of the lead body 620 can be combined with any of the above and below discussed embodiments.

Figure 6E:
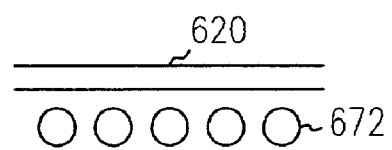
FIG. 6E is an enlarged cross section of a portion of the lead as shown in FIG. 6B.
Figure 6E:
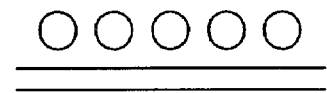
Figure 6F:
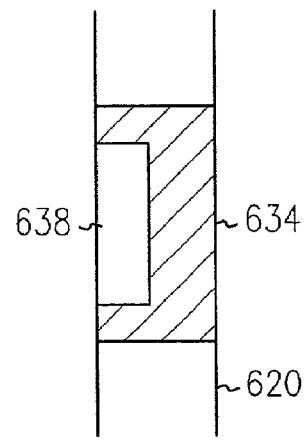
FIG. 6F is an enlarged cross section of a portion of the lead as shown in FIG. 6B.
Figure 6G:
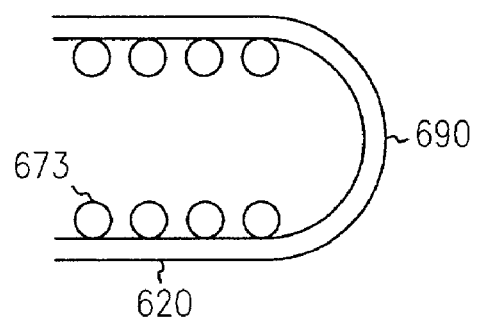
FIG. 6G is an enlarged cross section of a portion of the lead as shown in FIG. 6B.

FIG. 6C shows the side cross section of one embodiment of the lead 600 along line C-C of FIG. 6B. The lead 600 optionally has two sets of coils 672,673 at this portion. FIG. 6D shows a pacing electrode 632 in greater detail. The electrode 632 optionally is partially masked with the contact portion 636 facing outward, so that in an implanted site, the electrode 632 contacts the vascular tissue adjacent the myocardial wall. FIG. 6E shows the side cross section of the lead along line E-E of FIG. 6B, of a lead portion having one set of coils 672. FIG. 6F shows one embodiment of electrode 634 in greater detail, showing a partially masked electrode 634 with the contact portion 638 facing inward. FIG. 6G shows the side cross section of the lead 600 along line G-G of FIG. 6B showing the end tip 690 of the lead 600.

Figure 7:
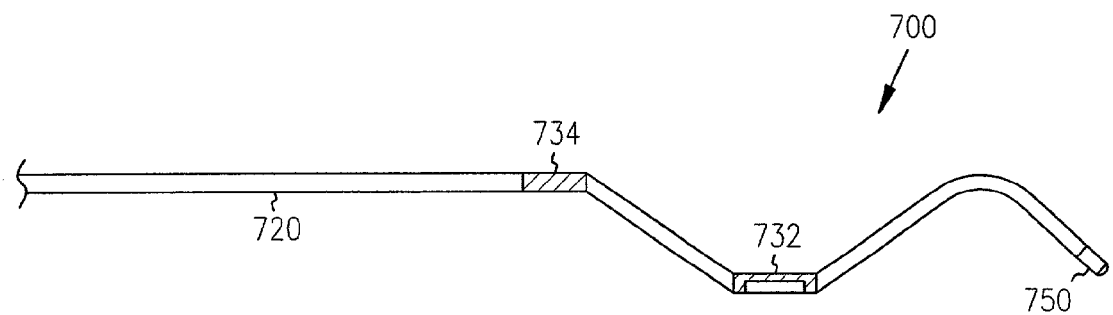
FIG. 7 is a side view of a coronary vein lead constructed in accordance with one embodiment.

FIG. 7 illustrates another option for a cardiac vein lead, for example, a multiple polar lead 700 adapted for use in a passageway, such as a cardiac vein. In one option, a third electrode 750 is added to a bipolar configuration, and the lead 700 can be used to pace and sense both the atrium and the ventricle. This configuration would allow the middle electrode 732 to be used as a common anode for both an atrial and ventricular bipole. This configuration would result in a lead utilizing the advantages of two bipole pairs with only three electrodes. In another option, the electrode 734 is electrically common with the electrode 750.

The lead 700 has a proximal end (as shown at 102 of FIG. 1), and attaches to a pulse sensor and generator (as shown at 140 of FIG. 1). The lead body 720 is cylindrical in shape and includes one or more electrical conductors. The electrical conductors are made of a highly conductive, highly corrosion-resistant material. The one or more electrical conductors carry current and signals between the pulse sensor and generator and the electrodes 732, 734 and 750. In one embodiment, the electrode 734, for example, a full ring electrode, serves as ground. The electrode 732 is a half ring electrode and serves as an atrial electrode. In another option, the electrode 750 is a PICOTIP (TM) electrode, and also comprises a ventricular electrode.

Figure 8:
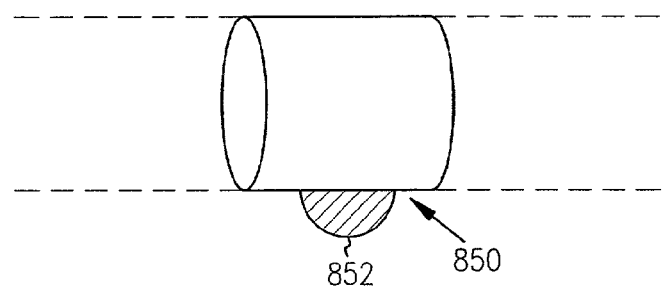
FIG. 8 is a side view of an electrode constructed in accordance with one embodiment of the coronary vein lead.

FIG. 8 shows a miniaturized high impedance PICOTIP (TM) electrode 850 constructed and arranged to be a side mounted electrode, which can be used with any of the leads discussed herein. This miniaturized electrode 850 increases electrode impedance by using a smaller exposed area. Electrode 850 comprises an electrode mesh 852 which increases chronic lead stability by providing local tissue ingrowth into the electrode mesh. In another embodiment, the PICOTIP (TM) electrode protrudes from the lead body to enhance intimate wall contact.

A lead according to the coronary vein leads described herein is implanted in any suitable manner, for example, as follows. Venous access is obtained via the subclavian, cephalic or jugular vein. A standard stylet is inserted into the lead to straighten it and provide stiffness for insertion of the lead into the vasculature. The coronary vein lead will then be guided into the coronary sinus/great cardiac vein. Once the coronary vein lead is positioned, the stylet will be removed. The preferred position for coronary vein lead placement is, in one option, to place the tip of the coronary vein lead near the origin of the great cardiac vein just proximal to the point where it originates from the interventricular vein. This will position the pacing electrodes near the end of the coronary sinus.

The lead is tested for P-wave, P/R ratio and atrial and ventricular threshold. The lead will be manipulated and repositioned to maximize P-Wave and P/R ratios, and minimize atrial voltage threshold. Target thresholds will be below 2.0 volts with a P-wave above 2 mVolts and a P/R ratio above 2. An optional method for implanting these leads is to use an "over the wire" method, for example, with an open lumen lead. This involves (1) placing a guide catheter into the coronary sinus (2) threading a guide wire into the coronary veins, and (3) pushing the lead over the guide wire.

Figure 9:
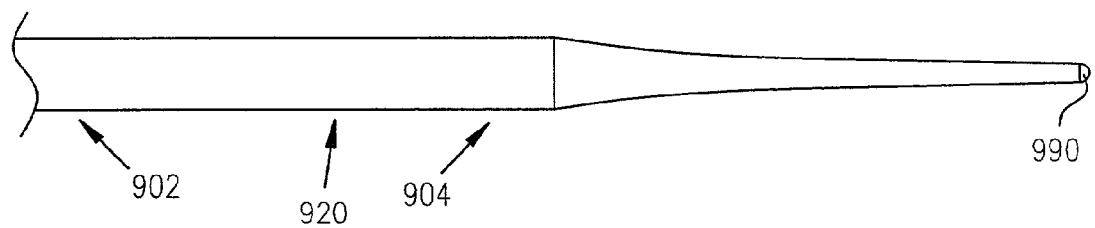
FIG. 9 is a side view of a coronary vein lead constructed in accordance with one embodiment.

Two other design features are described herein which improve the implantability and the chronic performance of leads. First, it was found that a slender distal tubing or stylet/conductor coil section was instrumental in improving the ability of the medical personnel to position these leads. It is believed that this feature provided the distal portion of the lead with a guiding means that easily followed the vasculature. This was accomplished only when the diameter of this guiding section was considerably less than that of the vasculature. In one embodiment shown at FIG. 9, a lead body 920 having a tapered flexible distal tip 990 at its distal portion 904 is shown which allows for easier access to distal veins. The outer diameter of the lead body 920 tapers from the proximal portion 902 to the distal tip 990 of the distal portion 904. The tapered lead body provides a smaller outer diameter at the distal tip 990, and allows more easy access to the distal veins, which have a decreasing inner diameter, and can be more complex. In one option, the taper of the lead body reduces the outer diameter by 30-70% at the distal tip 990.

Figure 10A:
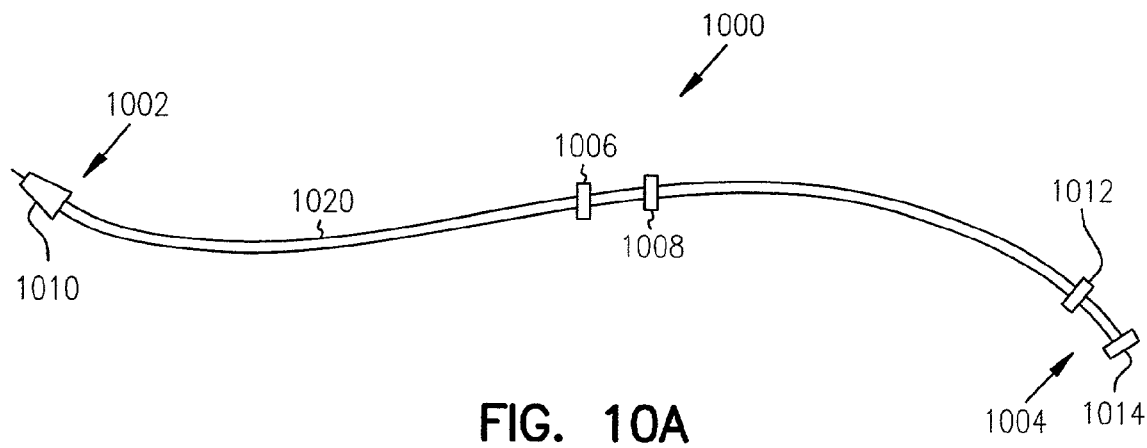
FIG. 10A is a side view of a coronary vein lead constructed in accordance with one embodiment.

Referring to FIG. 10A, a lead is shown generally at 1000. The lead 1000 provides ventricular pacing and sensing with or without atrial pacing and sensing. In another option, the lead 1000 provides atrial pacing and sensing with or without ventricular pacing and sensing. In yet another option, the lead 1000 provides ventricular pacing and sensing with or without sided defibrillation. The lead 1000 has a proximal end shown generally at 1002 and a distal end shown generally at 1004. The lead 1000 has a connector terminal 1010 at its proximal end and a lead body 1020, and is constructed and arranged for insertion into the coronary sinus. The lead 1000 attaches to a pulse sensor and generator. The lead body 1020 has multiple electrodes. Proximal ring electrodes 1006 and 1008 are provided for atrial or ventricular sensing and distal electrodes 1012 and 1014 are provided for ventricular sensing and pacing. Connector terminal 1010 electrically connects the various electrodes and conductors within the lead body to the pulse sensor and generator. The pulse sensor and generator also contains electronics to sense various pulses of the heart and also produce pulsing signals for delivery to the heart. The pulse sensor and generator 1040 also contains electronics and software necessary to detect certain types of arrhythmias and to correct for them. Physicians are able to program the pulse sensor and generator to correct a particular arrhythmia that the patient may have. It should be noted that there are numerous types of connector terminals which connect to a pulse sensing and generating unit 1040.

In use, the distal end 1004 of the lead 1000 is placed far enough into the coronary venous system to stimulate the ventricle, as shown for example, in FIG. 3B. This stimulation may occur at the base of the ventricle, the middle ventricle or the apex of the ventricle.

Figure 10B:
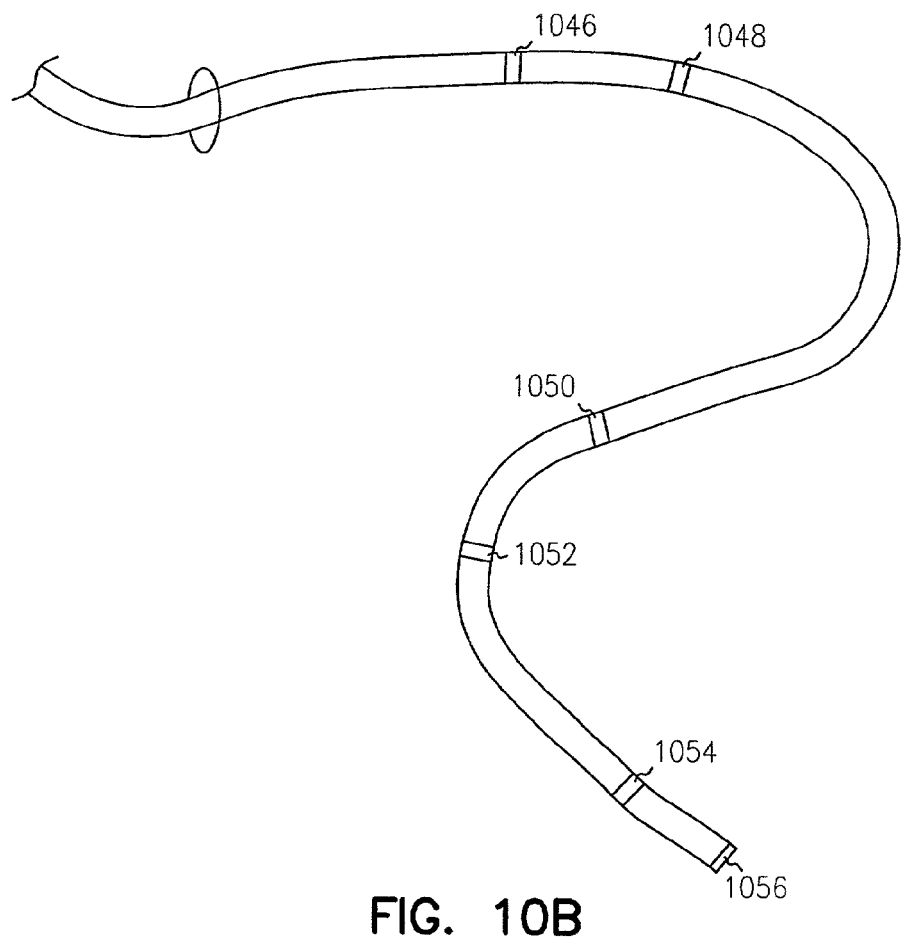
FIG. 10B is a side view of a coronary vein lead constructed in accordance with one embodiment.

In one embodiment, the lead 1000 is instantiated only for pacing and sensing purposes, and the lead 1000 may have unipolar or bipolar distal electrodes. Referring to FIG. 10B, in one embodiment, the lead 1000 has multiple pairs of distal electrodes for multisite ventricular pacing. Electrodes 1046 and 1048 form an electrode pair located in the coronary sinus/great cardiac vein, and electrodes 1050 and 1052 form an electrode pair located in the ventricular portion of the lead 1000, implanted in the coronary venous system. Electrodes 1054 and 1056 also form an electrode pair located on the ventricular portion of the lead 1000 implanted in the coronary venous system. The embodiment shown at FIG. 10B may have a lead body made of a biocompatible material having shape memory characteristics such that it will return to its preformed shape once implanted and a stylet or guidewire is removed. An example of such a material is polyether polyurethane. In addition, the lead body may have portions which have shape memory characteristics, comprising either a shape memory polymer or a shape memory metal.

In one embodiment, the lead 1000 has proximal electrodes, shown at 1006 and 1008 of FIG. 10A, which are either bipolar or unipolar, for sensing and/or pacing of the atrium. In one embodiment, multiple pairs or multiple sets of electrodes may be used for bi-atrial pacing. An optional distal electrode 1014 of the lead 1000 serves as a distal shocking electrode for the purpose of delivering a high energy shock greater than about 0.01 Joule to the ventricle. This distal shocking electrode may be added to any of the lead configurations disclosed herein.

Figure 11:
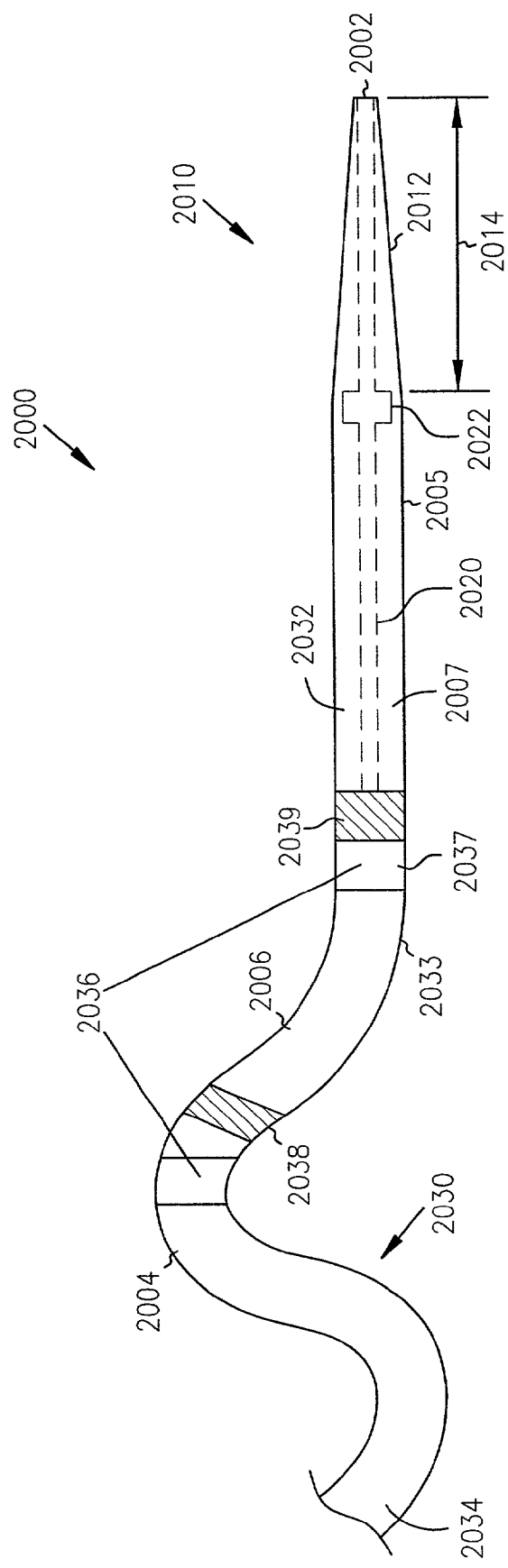
FIG. 11 illustrates a side elevational view of a portion of a lead with an atraumatic tip constructed in accordance with one embodiment.

A lead 2000 constructed in accordance with another embodiment is illustrated in FIG. 11. It should be noted that the lead 2000 and features thereof can be combined with the features discussed in the above described and illustrated embodiments. The lead 2000 comprises an open lumen lead, in one option. In another option, the lead 2000 is suitable for implantation within a body using a stylet, catheter, and/or guidewire. The lead 2000 has a lead body 2006 that extends to a distal end 2002, and has an atraumatic tip assembly 2010, as further described below. The lead 2000 includes a biased portion 2030 at an intermediate portion 2004 of the lead 2000, and a non-biased portion 2032 distal to the biased portion 2030.

The biased portion 2030 extends from a first end 2033 to a second end 2034. In one option, the biased portion 2030 has a two-dimensional bias. In another option, the biased portion 2030 has a three-dimensional bias, for example, a helical shape as discussed above (See e.g. FIGS. 3B and 3C). For instance, the biased portion 2030 has a helical shape with 1-2 turns. In yet another option, one or more biases are formed within the biased portion 2030. The biased portion 2030 is formed into a bias with, for example, shape memory material such that the lead body 2006 is straightened during implantation, and biased once implanted, for example, once the stylet is removed from the lead body 2006. One example of a suitable material, although not limited to such material, is polyether polyurethane. In another option, shape memory material for the conductor can be used, such that the conductor can be formed with a bias. The biased portion 2030 assists in maintaining the lead 2000 within a passage, such as a cardiac vein or an artery. In addition, the biased portion 2030 assists in enhancing tissue-electrode contact.

The lead 2000 further includes one or more electrodes 2036. For example, in one option, the one or more electrodes 2036 are disposed on the lead body 2006 along the biased portion 2030, where the biased portion 2030 would assist in fixation of the one or more electrodes 2036 and/or enhance tissue contact. In another option, the one or more electrodes 2036 are disposed 120 degrees apart along the biased portion 2030, which increases the opportunity for the electrodes 2036 to make contact with the myocardial wall. In another option, a steroid collar 2038 is disposed directly adjacent to the one or more electrodes 2036, for example, along the biased portion 2030. The biased portion 2030 further enhances the effectiveness of the steroid collar 2038 by biasing a portion of the steroid collar 2038 toward the tissue. In yet another option, the lead 2000 further includes another electrode 2037 along the non-biased portion 2032, and optionally another steroid collar 2039 directly adjacent to the electrode 2037.

As discussed above, the lead 2000 includes an atraumatic tip assembly 2010. The atraumatic tip assembly 2010 includes a flexible portion that is significantly more flexible than the biased portion 2030. In one option, the flexible portion includes the tapered portion 2012. This allows for improved maneuverability of the lead 2000 through tortuous vasculature, and allows for the lead 2000 to be implanted more easily and quickly than conventional leads. Furthermore, the flexible tapered portion 2012 allows for the guidewire, if used, to better guide the lead 2000 without interference from the biased portion 2030. In one option, the flexible portion is premolded and bonded to the remaining portion of the lead 2000 that forms a sub-assembly. In another option, the subassembly is placed within a mold, and the remaining portion of the lead 2000 is molded thereon.

The tapered portion 2012 begins, in one option, at the distal end 2002 of the lead body 2006 and extends to the intermediate portion 2004 of the lead 2000 and ends at 2005. Disposed between 2005 and the biased portion 2030 is a portion 2007 that extends, in one option, for a length of 5-10 cm, which further assists in the maneuverability of the lead 2000. In another option, the tapered portion 2012 begins at the distal end 2002 of the lead body 2006 and extends until the biased portion 2030 of the lead body 2006. The length 2014 of the tapered portion 2012, in another option, is 1-2 cm. The tapered portion 2012 assists in allowing for the lead body 2006 to more easily traverse vessels that generally narrow, make tight turns, and frequently branch off. It should be noted that the flexible portion can have a length that is different than the tapered portion 2012.

Figure 12:
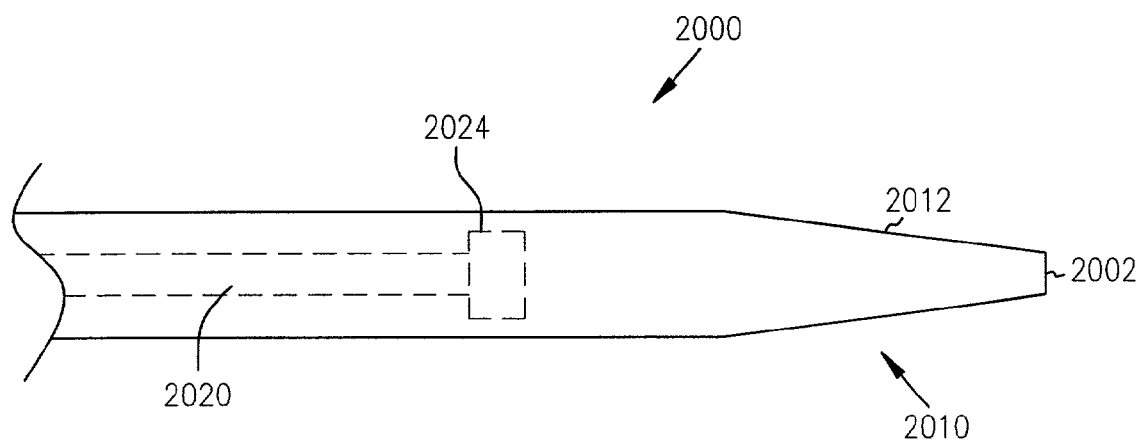
FIG. 12 illustrates a side elevational view of a portion of a lead with an atraumatic tip constructed in accordance with one embodiment.

The lead 2000 further includes at least one conductor 2020. The at least one conductor 2020, in one option, does not extend to the distal end 2002 of the lead body 2006. In another option, the at least one conductor 2020 terminates between the most distal electrode and the distal end 2002 of the lead body 2006. This allows for enhanced flexibility of the atraumatic tip assembly 2010, where the distal portion includes all, for example, rubber material without any rigidity from the conductors. The conductor further assists in the transition, and the flexibility between the intermediate lead body and the tapered portion of the lead portion. In one option, the at least one conductor 2020 terminates at 2022 along a portion of the tapered portion 2012 of the lead body 2006. In another option, the at least one conductor 2020 terminates at 2024, that is proximal to the tapered portion 2012, as shown in FIG. 12. In this configuration, no conductor 2020 would be present along the tapered portion 2012, allowing for enhanced flexibility of the tapered portion 2012. In another option, the conductor 2020 comprises one or more coiled wires, having an inner diameter. The inner diameter, optionally, is isodiametric along the entire length of the conductor 2020, providing for further options with respect to flexibility for the atraumatic tip assembly 2010

Figure 13:
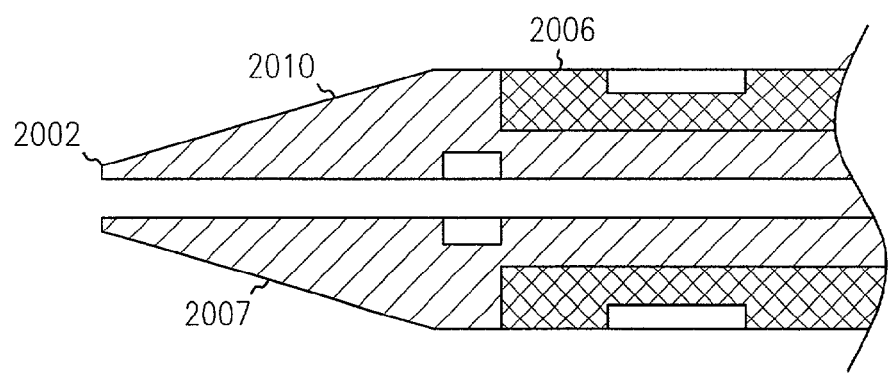
FIG. 13 illustrates a cross-sectional view of a portion of a lead with an atraumatic tip constructed in accordance with one embodiment.

During placement of a lead, a physician will often use the distal end of the conductor under fluoroscope to determine the placement of the lead within a patient. However, given the new atraumatic tip assembly 2010 as shown in FIG. 11, a physician may not be able to rely on this to establish the location of the distal end of the lead 2000. Thus, the lead 2000 further includes, in one option, radiopaque materials within the lead body 2006, for example incorporated into the lead body 2006 at the distal end 2002 of the lead body 2006. In another option, a pre-molded tip assembly is formed of rubber, or other flexible material, filled with radiopaque material, where optionally the entire tapered portion is formed of the filled material 2007, as shown in FIG. 13. The lead body 2006 is formed of a flexible material, such as, but not limited to, LSR or Gumstock. Examples of radiopaque materials include, but are not limited to, barium sulfate, bismuth subcarbonate, tungston powder, platinum powder, platinum/iridium alloy powder, or a Pt Ir marker band. Varying the material selection of the lead body 2006 for the atraumatic tip assembly 2010 will allow for providing a more flexible atraumatic tip assembly 2010. Wall thicknesses for embodiments including radiopaque materials may need to be increased from above-discussed embodiments. In addition, having the radiopaque material at the distal end 2002 of the lead body 2006 will allow for a physician to more accurately determine the location of the lead 2000 within a passage of a body.

The lead advantageously allows for effective use of a biased portion on a lead body in combination with an atraumatic tip assembly. The biased portion allows for gentle and effective forces against passage walls enabling the lead to be positionally maintained therein. In addition, the biased portion ensures the electrode is placed up against the passage wall with sufficient force. The spacing of the electrodes along the biased portion provides for an increased opportunity for the electrode to be placed against the passage wall. The atraumatic tip assembly is extremely flexible, relative to the biased portion, which allows for improved maneuverability of the lead through tortuous vasculature, and allows for the lead to be implanted more easily and quickly than conventional leads. Furthermore, the flexible tapered portion of the atraumatic tip assembly allows for the guidewire or stylet, if used, to better guide the lead without interference from the biased portion.

The leads described herein provide several advantages over previous leads. The leads provide, in one option, the ability to sense and pace the heart using leads positioned within the cardiac vasculature, and further the leads provide the ability to pace and/or sense the left heart. It has been found that by placing a therapeutic lead near the atrium, but not in the atrium, higher amplitude electrograms may be detected as compared to a standard endocardial lead. Further, it has been found that left sided pacing may help suppress atrial arrhythmias, particularly those originating near the left atrium. Still further, it has been found that the ability to critically control the timing between pacing the atria and ventricles of the heart is of utility in optimizing pacing therapies. The leads described herein involve geometries that utilize the shape of the local vasculature, the shape of the heart, or both, to help insure that an optimally positioned lead will remain in that position well beyond the time of implant. The lead designs discussed herein yield reliable and optimal performance in sensing and pacing of the heart. New coronary lead configurations are provided which can provide dual chamber pacing and/or defibrillation on a single lead body.

Further provided herein is a method for placing a lead into a coronary vein to provide sensing and pacing of the heart, for example, the left side of the heart. In one embodiment, a lead is provided that is a right side lead and is placed within the coronary sinus, and is then advanced from the coronary sinus toward the left atrium to provide left sided sensing and pacing.

In another embodiment, a method includes placing a guidewire within one or more passageways of a body, and threading a lead assembly over the guidewire. It should be noted that the lead assembly can be threaded over the guidewire first, and then placed in a patient, or vice versa. The lead assembly includes a lead body adapted to carry signals, where the lead body has a proximal end and a distal end, and an intermediate portion therebetween. The lead assembly further includes a connector located at the proximal end of the lead body, and at least one conductor is disposed within the lead body. The lead body has at least one preformed biased portion at an intermediate portion of the lead body, and a flexible portion and a tapered portion are disposed between the biased portion and the distal end of the lead body. The tapered portion is distal to the biased portion and is more flexible than the biased portion. The method further includes biasing one or more electrodes against a wall of at least one of the passageways, and placing the distal end in a cardiac vein.

Several options for the method are as follows. For instance, in one option, the method further includes viewing the distal tip assembly under fluoroscopy, where the lead assembly includes a distal tip assembly including a premolded portion filled with radiopaque material. In another option, the method further includes flexing the distal end of the lead body. Optionally, biasing the electrodes against the wall of the passageway includes positioning one or more electrodes around a helical portion of the lead body.

It is to be understood that the above description is intended to be illustrative, and not restrictive. Many other embodiments will be apparent to those of skill in the art upon reading and understanding the above description. It should be noted that embodiments discussed in different portions of the description or referred to in different drawings can be combined to form additional embodiments of the present invention. The scope of the invention should, therefore, be determined with reference to the appended claims, along with the full scope of equivalents to which such claims are entitled.

What is claimed is:

1. A lead assembly for coupling to an implantable pulse generator, the lead assembly comprising:
   a lead body adapted to carry signals, the lead body having a proximal end and a distal end, and an intermediate portion therebetween;
   a connector located at the proximal end of the lead body for coupling the lead assembly to the implantable pulse generator;

at least one conductor disposed within the lead body;
the lead body having at least one preformed biased portion at an intermediate portion of the lead body, the biased portion constructed and arranged to fixate against an interior wall of a coronary vessel upon implantation;
a first unbiased portion disposed adjacent a proximal end of the biased portion;
a second unbiased portion disposed adjacent a distal end of the biased portion, the second unbiased portion including a flexible tapered portion substantially more flexible than the biased portion and adapted to be implanted within a passage, the flexible tapered portion terminating at a distal tip of the lead body;
an open lumen extending longitudinally through the distal tip of the lead body such that the lead can be threaded over a guidewire during implantation of the lead; and
at least a first and a second electrode coupled with the at least one conductor and disposed on the biased portion.

2. The lead assembly as recited in claim 1, wherein the conductor forms an inner lumen therein, and the inner lumen is isodiametric from the proximal end to a position near the distal end of the lead body.

3. The lead assembly as recited in claim 1, wherein none of the conductors extend to the distal end of the lead body.

4. The lead assembly as recited in claim 3, wherein the conductor terminates within the second unbiased portion of the lead body.

5. The lead assembly as recited in claim 1, wherein the biased portion includes a helical shape having a lateral width less than about 2 cm.

6. The lead assembly as recited in claim 5, wherein the at least first and second electrodes are disposed along the helical shape and are spaced 120 degrees apart relative to one another as measured from an axis of the helical shape.

7. The lead assembly as recited in claim 1, further comprising radiopaque material molded within material forming the flexible tapered portion of the second unbiased portion.

8. The lead assembly as recited in claim 1, wherein the second unbiased portion extends from the biased portion to the distal end of the lead body and includes a length of about 5 cm or more.

9. The lead assembly as recited in claim 8, wherein the flexible tapered portion of the second unbiased portion extends for a predetermined length, where the predetermined length is about 2 cm or less.

10. The lead assembly as recited in claim 1, further comprising a third electrode and a drug collar disposed on the second unbiased portion, the third electrode set back at least about 2 cm from the distal end of the lead body.

11. A lead assembly for coupling to an implantable pulse generator, the lead assembly comprising:
a lead body adapted to carry signals, the lead body extending from a proximal end to a distal end, and an intermediate portion therebetween, the lead body terminating at a distal tip;
a connector located at the proximal end of the lead body for coupling the lead assembly to the implantable pulse generator;
at least one conductor disposed within the lead body;
the lead body having at least one preformed biased portion at an intermediate portion of the lead body, the biased portion constructed and arranged to fixate against an interior wall of a coronary vessel upon implantation and including a length of about 3 cm or more;
an unbiased portion disposed adjacent a distal end of the biased portion, the second unbiased portion including a flexible portion and a tapered portion near the distal end of the lead body, the flexible portion is more flexible than the biased portion and the tapered portion adapted to be implanted within a passage;
an open lumen extending longitudinally through the distal tip of the lead body such that the lead can be threaded over a guidewire during implantation of the lead; and
at least a first and a second electrode coupled with the at least one conductor and disposed on the biased portion.

12. The lead assembly as recited in claim 11, wherein the tapered portion extends from the distal tip.

13. The lead assembly as recited in claim 11, wherein the flexible portion extends from the distal tip to a portion between the biased portion and the distal tip.

14. The lead assembly as recited in claim 11, wherein the flexible portion is premolded and bonded to the intermediate portion of the lead body, the flexible portion extending from the distal tip to the preformed biased portion.

15. The lead assembly as recited in claim 11, wherein radiopaque material is molded within the entire tapered portion.

16. The lead assembly as recited in claim 11, wherein the flexible portion has a length greater than the tapered portion.

17. The lead assembly as recited in claim 11, wherein the at least one conductor does not extend to the distal tip.

18. The lead assembly as recited in claim 11, wherein the biased portion includes a helical shape having a lateral width less than about 2 cm.

19. The lead assembly as recited in claim 18, wherein the at least first and second electrodes are disposed along the biased portion and are spaced about 120 degrees apart around the helical shape as measured from an axis of the helical shape.

20. The lead assembly as recited in claim 11, further comprising an electrical stimulation device coupled with the lead body.

21. A lead assembly for coupling to an implantable pulse generator, the assembly comprising:
a lead body adapted to carry signals, the lead body extending from a proximal end to a distal end, and an intermediate portion therebetween, the lead body terminating at a distal tip;
a connector located at the proximal end of the lead body for coupling the lead assembly to the implantable pulse generator;
at least one conductor disposed within the lead body;
the lead body having at least one preformed biased portion at an intermediate portion of the lead body for fixation within a vessel, the biased portion having a lateral width less than about 2 cm and including two or more electrodes disposed thereon; and
an unbiased portion disposed distal to the biased portion, the unbiased portion having a length of about 5 cm or more and including a flexible portion and a tapered portion,
the flexible portion disposed near the distal end of the lead body and more flexible than the biased portion,
the tapered portion disposed at the distal end of the lead body and adapted to be implanted within a passage; and
an open lumen extending longitudinally through the distal tip of the lead body such that the lead can be threaded over a guidewire during implantation of the lead.

22. The lead assembly as recited in claim 21, wherein the flexible portion extends from the distal tip.

23. The lead assembly as recited in claim 21, wherein the flexible portion extends from the distal tip to a portion between the biased portion and the distal tip.

24. The lead assembly as recited in claim 21, wherein the flexible portion extends from the distal tip to the biased portion.

25. The lead assembly as recited in claim 21, wherein the lead body has a tapered portion extending from the distal tip, and the tapered portion extends from the distal tip to a portion between the biased portion and the distal tip.

26. The lead assembly as recited in claim 21, wherein the distal end of the lead body includes a premolded tip assembly filled with radiopaque material.

27. The lead assembly as recited in claim 21, where the biased portion includes a preformed helical portion.

28. A method of implanting a lead assembly for use in combination with an implanted pulse generator, the method comprising:

placing a guidewire within a coronary vein of a patient's body;

threading the lead assembly over the guidewire after placing the guidewire in the coronary vein, the lead assembly including a lead body adapted to carry signals, the lead body having a proximal end and a distal end, and an intermediate portion therebetween, a connector located at the proximal end of the lead body, at least one conductor disposed within the lead body, the lead body having at least one preformed biased portion at an intermediate portion of the lead body, the biased portion constructed and arranged to fixate against an interior wall of a coronary vessel upon implantation, an unbiased portion disposed adjacent a distal end of the biased portion, the second unbiased portion including a flexible portion and a tapered portion disposed between the biased portion and the distal end of the lead body, the tapered portion is distal to the biased portion and is more flexible than the biased portion, and at least a first and a second electrodes coupled with at least one conductor and disposed on the biased portion;

removing the guidewire so as to allow the biased portion to return to its original shape thereby biasing the at least first and second electrode against the interior wall of the coronary vessel; and connecting the lead assembly to the pulse generator.

29. The method as recited in claim 28, wherein the lead assembly includes a distal tip assembly including a premolded portion filled with radiopaque material, and further comprising viewing the distal tip assembly under fluoroscopy.

30. The method as recited in claim 28, further comprising flexing the distal end of the lead body, including flexing the unbiased portion having a length of about 5 cm or more.

31. The method as recited in claim 28, wherein biasing the electrodes against the interior wall of the coronary vessel includes positioning the at least first and second electrodes around a helical portion of the lead body having a lateral width of about 2 cm or less.

* * * * *

UNITED STATES PATENT AND TRADEMARK OFFICE
CERTIFICATE OF CORRECTION

| | |
|---|---|
| PATENT NO. | : 7,628,801 B2 |
| APPLICATION NO. | : 10/128997 |
| DATED | : December 8, 2009 |
| INVENTOR(S) | : Westlund et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 957 days.

Signed and Sealed this

Second Day of November, 2010

David J. Kappos
*Director of the United States Patent and Trademark Office*